(12) United States Patent (10) Patent No.: US 7,983,771 B2
Boukhny et al. (45) Date of Patent: Jul. 19, 2011

(54) GRAPHICAL USER INTERFACE INCLUDING A POP UP WINDOW FOR AN OCULAR SURGICAL SYSTEM

(75) Inventors: Mikhail Boukhny, Laguna Niguel, CA (US); David Thoe, Aliso Viejo, CA (US); Nam (Gus) H. Tran, Irvine, CA (US)

(73) Assignee: Novartis AG, Basel (CH)

( * ) Notice: Subject to any disclaimer, the term of this patent is extended or adjusted under 35 U.S.C. 154(b) by 1745 days.

(21) Appl. No.: 11/193,159

(22) Filed: Jul. 29, 2005

(65) Prior Publication Data

US 2006/0248477 A1 Nov. 2, 2006

Related U.S. Application Data

(63) Continuation-in-part of application No. 11/170,952, filed on Jun. 30, 2005.

(60) Provisional application No. 60/671,879, filed on Apr. 15, 2005, provisional application No. 60/631,738, filed on Nov. 30, 2004.

(51) Int. Cl.
*G05B 15/00* (2006.01)
*G06F 3/048* (2006.01)
*A61B 1/04* (2006.01)
*A61B 17/20* (2006.01)

(52) U.S. Cl. .......... 700/83; 715/784; 715/830; 715/973; 600/126; 604/22

(58) Field of Classification Search .............. 700/11–16, 700/83, 87, 90; 600/126; 604/22, 120; 715/700, 715/784–787, 830, 973; 345/23, 24, 173; 702/89, 104
See application file for complete search history.

(56) References Cited

U.S. PATENT DOCUMENTS 4,812,996 A 3/1989 Stubbs
(Continued)

FOREIGN PATENT DOCUMENTS

EP 1837002 A2 9/2007
(Continued)

OTHER PUBLICATIONS

European Patent Application No. 06112599.3 (with Search Report), Publication No. 1712211 Al; 37 pages.
(Continued)

*Primary Examiner* — Sean P Shechtman

(57) ABSTRACT

A graphical user interface for use in an ocular surgical system, such as phacoemulsification and vitreo-retinal surgical systems. A display screen shows a display element that includes a representation of a parameter of pulses generated by the ocular surgical system relative to a position of the controller. A window is displayed on the display screen and generated in response to touching the display screen of the ocular surgical system. The window includes a display element having a value of a parameter of the system. A value of the parameter is changed by touching the display screen at the adjustment element. The window can also include a representation of the parameter of the pulses relative to the position of the controller and an adjustment element for changing a value of the parameter represented in the display element. The representation in the window can be linear or non-linear, indicating the function of the parameter relative to a position of a controller, such as a foot pedal. A current representation of the parameter displayed in the window is changed to a different representation of the parameter in response to touching the display screen at the window. The window is closed by touching the display screen at a pre-defined area of the window. The window can also be configured to fade away or close after a pre-determined amount of time of inactivity or in response to a user.

37 Claims, 20 Drawing Sheets

U.S. PATENT DOCUMENTS

| | | | |
|---|---|---|---|
| 4,933,843 | A | 6/1990 | Scheller et al. |
| 5,249,121 | A | 9/1993 | Baum et al. |
| 5,371,851 | A | 12/1994 | Pieper et al. |
| 5,455,766 | A | 10/1995 | Scheller et al. |
| 5,554,894 | A | 9/1996 | Sepielli |
| 5,580,347 | A | 12/1996 | Reimels |
| 5,853,367 | A | 12/1998 | Chalek et al. |
| 5,877,957 | A | 3/1999 | Bennett |
| 5,898,434 | A | 4/1999 | Small et al. |
| 5,910,139 | A | 6/1999 | Cochran et al. |
| 5,997,528 | A | 12/1999 | Bisch et al. |
| 6,066,129 | A | 5/2000 | Larson |
| 6,106,512 | A | 8/2000 | Cochran et al. |
| 6,179,829 | B1 | 1/2001 | Bisch et al. |
| 6,251,113 | B1 | 6/2001 | Appelbaum |
| 6,319,220 | B1 | 11/2001 | Bylsma |
| 6,366,300 | B1 * | 4/2002 | Ohara et al. .................. 715/771 |
| 6,428,508 | B1 | 8/2002 | Ross |
| 6,442,440 | B1 | 8/2002 | Miller |
| 6,507,796 | B2 | 1/2003 | Alexander |
| 6,512,530 | B1 | 1/2003 | Rzepkowski et al. |
| 6,583,796 | B2 | 6/2003 | Jamar et al. |
| 6,628,996 | B1 * | 9/2003 | Sezaki et al. .................... 700/83 |
| 6,659,998 | B2 | 12/2003 | DeHough et al. |
| 6,671,535 | B1 | 12/2003 | McNichols et al. |
| 6,707,474 | B1 | 3/2004 | Beck et al. |
| 6,783,523 | B2 | 8/2004 | Qin et al. |
| 7,077,820 | B1 | 7/2006 | Kadziauskas et al. |
| 7,225,405 | B1 | 5/2007 | Barrus et al. |
| 2002/0045887 | A1 | 4/2002 | DeHoogh |
| 2002/0054144 | A1 | 5/2002 | Morris-Yates |
| 2003/0073980 | A1 | 4/2003 | Finlay et al. |
| 2003/0137535 | A1 * | 7/2003 | Heo .............................. 345/741 |
| 2003/0195462 | A1 | 10/2003 | Mann et al. |
| 2004/0024384 | A1 | 2/2004 | Novak |
| 2004/0092922 | A1 | 5/2004 | Kadziauskas et al. |
| 2005/0080348 | A1 | 4/2005 | Stahmann et al. |
| 2006/0074405 | A1 | 4/2006 | Malackowski et al. |
| 2006/0114175 | A1 | 6/2006 | Boukhny |
| 2006/0235307 | A1 | 10/2006 | Boukhny et al. |
| 2006/0236242 | A1 | 10/2006 | Boukhny et al. |
| 2006/0248477 | A1 | 11/2006 | Boukhny et al. |
| 2007/0056596 | A1 | 3/2007 | Fanney et al. |
| 2007/0073214 | A1 | 3/2007 | Dacquay et al. |
| 2007/0078379 | A1 | 4/2007 | Boukhny et al. |
| 2009/0049397 | A1 | 2/2009 | Boukhny |

FOREIGN PATENT DOCUMENTS

| | | | |
|---|---|---|---|
| EP | 1835872 | B1 | 7/2008 |
| EP | 1712210 | B1 | 3/2009 |
| EP | 1712209 | B1 | 4/2009 |
| EP | 1837002 | A3 | 4/2009 |
| EP | 1712211 | B1 | 6/2009 |
| WO | WO 96/13216 | | 5/1996 |
| WO | WO 98/08442 | | 3/1998 |
| WO | WO 98/25556 | A1 | 6/1998 |
| WO | WO 02/32354 | | 4/2002 |
| WO | WO 2006/060423 | A1 | 6/2006 |

OTHER PUBLICATIONS

European Patent Application No. 06112596.9 (with Search Report), Publication No. 1712210 A1; 32 pages.

European Patent Application No. 06112595.1 (with Search Report), Publication No. 1712209 A1; 23 pages.

* cited by examiner

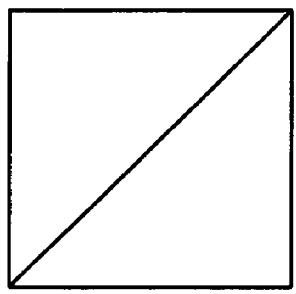
610
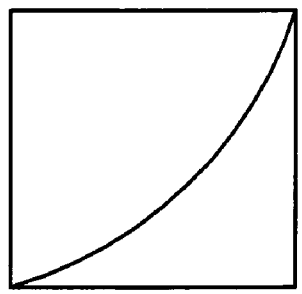
640
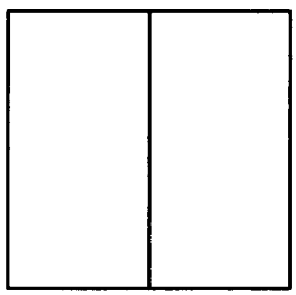
620
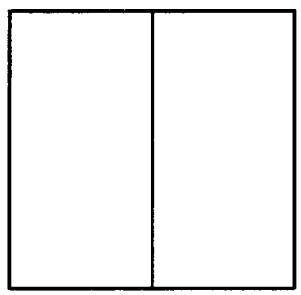
620
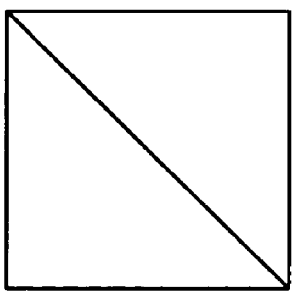
600
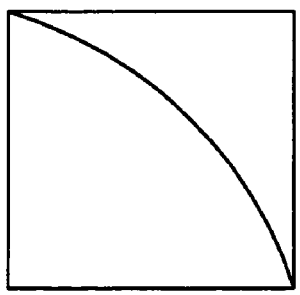
630
Fig. 6

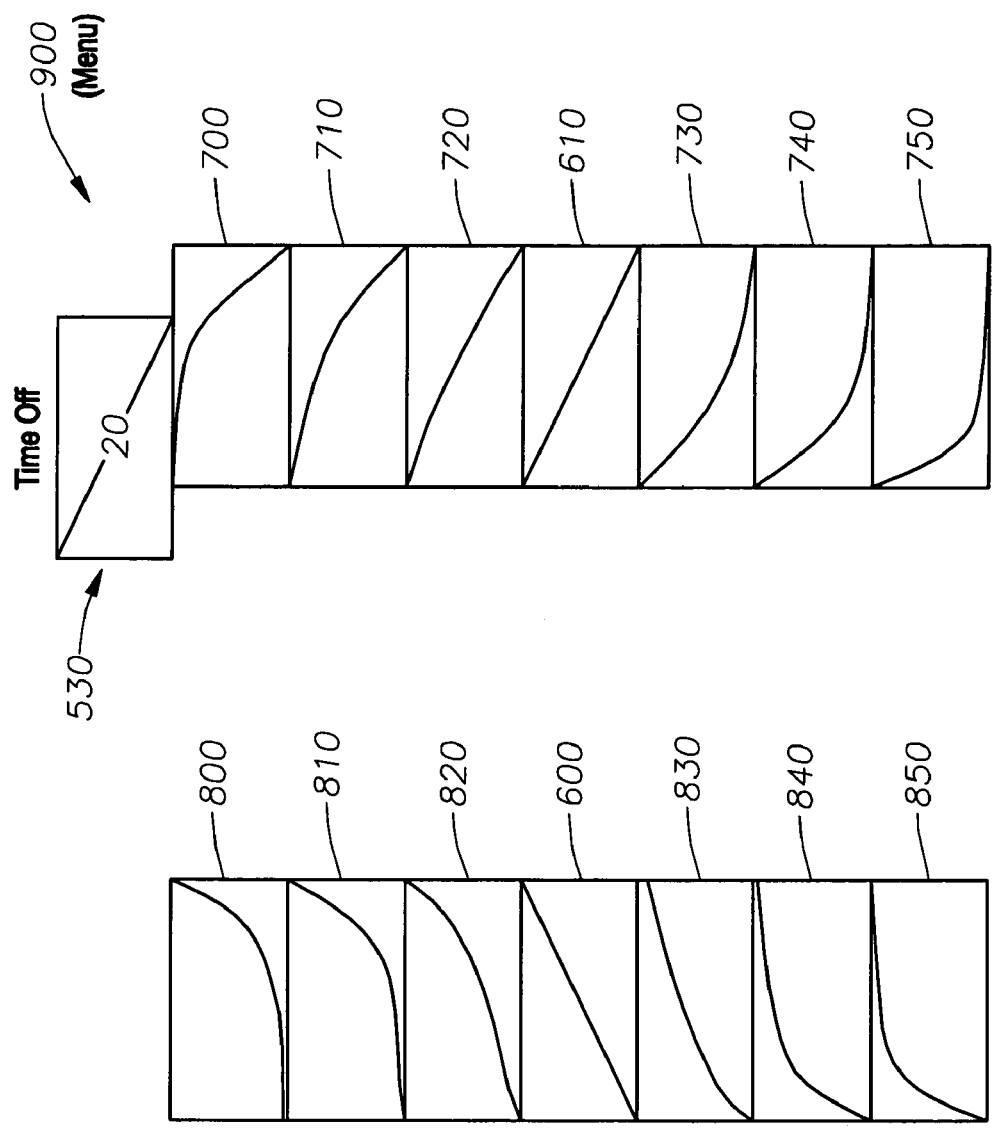
Fig. 9
Fig. 8
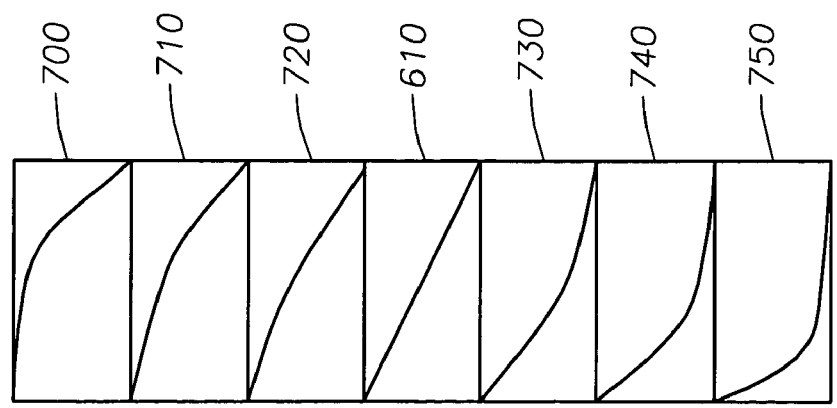
Fig. 7

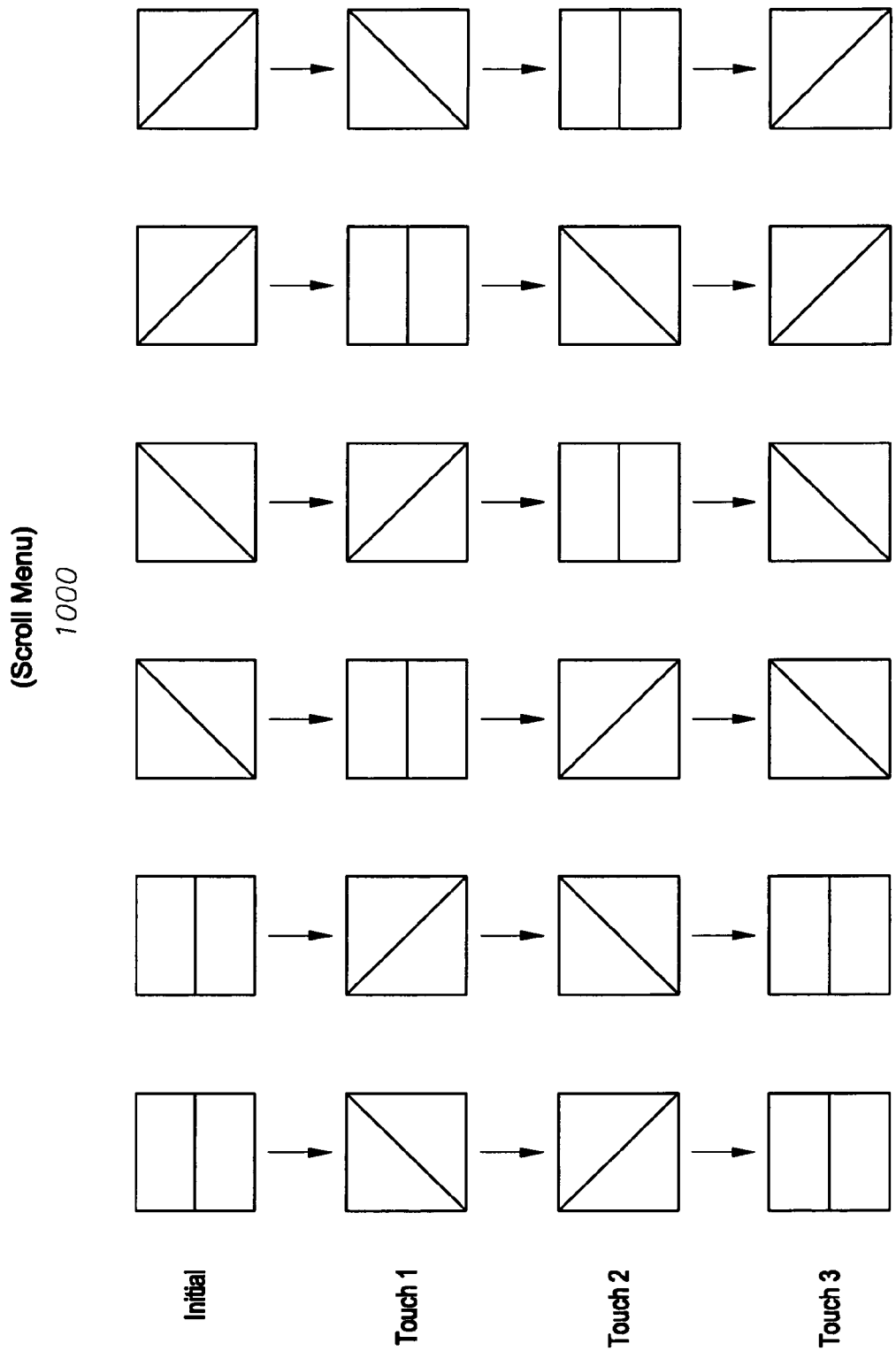

GRAPHICAL USER INTERFACE INCLUDING A POP UP WINDOW FOR AN OCULAR SURGICAL SYSTEM

CROSS REFERENCE TO RELATED APPLICATIONS

This application is a Continuation-In-Part (CIP) of co-pending U.S. application Ser. No. 11/170,952, filed Jun. 30, 2005, priority of which is claimed under 35 U.S.C. §120, the contents of which are incorporated herein by reference. This application also claims priority under 35 U.S.C. §119 to U.S. Provisional Patent Application No. 60/671,879 filed Apr. 15, 2005, and to U.S. Provisional Patent Application No. 60/631,738 filed Nov. 30, 2004, the contents of which are incorporated herein by reference.

TECHNICAL FIELD OF THE INVENTION

The invention relates generally to graphical user interfaces for surgical systems, and, more particularly, to graphical user interfaces for ocular surgical systems, such as phacoemulsification and vitreo-retinal surgical systems, that include a separate pop-up or dialog window to adjust a parameter of system.

BACKGROUND OF THE INVENTION

Modern ocular surgical systems, and in particular, modern ophthalmic and vitro-retinal surgical systems, for example, are designed to monitor and display multiple parameters of a surgical device or instrument that is connected to the surgical system and controlled by the surgeon through the use of a foot pedal. Such systems can be complex given the multiple parameters that must be displayed and controlled by a surgeon, particularly during a surgical procedure.

Certain known ocular surgical systems allow for application of ultrasound energy at a fixed level. For example, in a phacoemulsification surgical system, the foot pedal acts as an on/off switch to activate and deactivate ultrasound energy that is at a particular power level. When the foot pedal is pressed, the device is activated and the power level is constant and without interruptions, that is "continuous." Continuous power is approximately proportional to the amount of voltage applied to the piezoelectric crystals in the handpiece.

"Continuous" power systems were improved by the introduction of "linear" mode, which allows a surgeon to control power in a variable manner. A surgeon controls power based on the foot pedal position so that the power is proportional to or linear with respect to the displacement of the foot pedal. Thus, more power is provided as the surgeon presses the foot pedal, and less power is provided as the foot pedal is released. Further improvements involved the introduction of "pulse" mode. In "pulse" mode, energy is provided in periodic pulses at a constant duty cycle. The surgeon increases or decreases the amount of power by pressing or releasing the foot pedal, which increases or decreases the amplitude of the fixed-width pulses. Further enhancements involved the introduction of "burst" mode. In "burst" mode, power is provided through a series of periodic, fixed width, constant amplitude pulses. Each pulse is followed by an "off" time. The off-time is varied by the surgeon by pressing and releasing the foot pedal.

In order to accommodate continuous, "linear," "pulse" and "burst" mode and their operating parameters, known user interfaces of ocular surgical systems typically include several human actionable controllers and fields or elements that occupy particular positions on a display screen. Some known user interfaces include buttons, arrows, switches, bars and/or knobs for setting desired numeric values of operating characteristics of the surgical system. Certain parameters are fixed or have a constant value regardless of the foot pedal position, whereas other parameters vary, e.g., vary linearly, with the foot pedal. The interface is manipulated by a surgeon to provide control signals to the surgical instruments which, in turn, control the modes or types of pulses that are generated.

FIGS. 1 and 2 illustrate one known interface for a phacoemulsification surgical system. A surgeon manually selects the power mode from a selection bar or menu 10. In this interface, the menu 10 includes "Ultrasound Continuous," "Ultrasound Pulse," and "Ultrasound Burst" menu bars 12, 14 and 16, respectively. In the example illustrated in FIGS. 1 and 2, the continuous power menu bar 12 is selected from the menu 10. The power limit is represented in a field 20. The maximum amount of continuous power or the power limit is adjusted using up/down arrows 24. In this example, the continuous power limit is selected to be "35" or 35% of the maximum allowed power. The continuous power varies linearly, as shown by the line 26 in the background of the power limit field 20 up to a maximum value of 35%. The current power level is provided in a field 28. In the illustrated example, the current power is "0" or 0% in this example since the screen represents current power when the foot pedal is released. Pressing the foot pedal results in power increasing linearly from 0% to 35%. When the surgeon wants to change from "continuous" mode to another mode, the surgeon selects the "ultrasound continuous" bar 12 so that the menu 10 of available pulse modes is displayed. The surgeon can then select another mode from the menu 10.

Application of periodic ultrasound pulses can be described based on power, the duration of the pulses, the "On" or active time, and the duration of "Off" time or the duration between pulses. Alternatively, pulses can be specified using pulse rate and duty cycle. Pulse rate is the number of pulses contained in unit time. Duty cycle is the portion of the ultrasound cycle when the ultrasound is active. In other words, duty cycle is the ratio of On/(On+Off).

FIG. 3 illustrates "Ultrasound Pulse" menu bar 14 being selected from the menu 10. A surgeon manually selects a maximum power level of 35%, which varies linearly as the foot pedal is pressed and released. In addition, the interface includes a field 30 for the pulse rate or pulses per second (pps) and a field 40 for the "on-time" (% Time on). The number of pulses per second (pps) and the on-time, however, do not vary with movement of the foot pedal. Rather, the pps is fixed at 14 pps using arrows 34, and the on-time is fixed at 45% using arrows 44. Thus, the pps and on-time values do not change when the foot pedal is displaced and must be manually adjusted by the surgeon using arrows 34 and 44. Power increases linearly from 0-35% as the foot pedal is pressed, and is delivered at a fixed rate of 14 pulses per second at a fixed 45% duty cycle.

Referring to FIGS. 2 and 4, when "Ultrasound Burst" mode is selected from the menu 10, the same limit and power field 28 and limit field 20 are provided. The power varies linearly with the foot pedal, as discussed above. Rather than pps and on time fields 30 and 40 (as shown in FIG. 3), the interface displays a field 50 for on-time or On (ms) and a field 60 for off time or Off (ms) when in "burst" mode. The On (ms) value is fixed and does not change when the foot pedal is moved. The on-time (ms) is shown fixed at 70 ms and can be adjusted using arrows 54. The Off time decreases from a value to 0 ms with the foot pedal displacement. In this "burst" mode, the power increases from 0-40% as the foot pedal is depressed by changing the "off-time", and the duration of each pulse remains a constant 70 ms throughout displacement of the foot pedal.

While known interfaces have been successfully used to perform phacoemulsification and vitreo-retinal surgical procedures in the past, they can be improved. Particularly, the visual and functional aspects of interfaces can be enhanced so that surgeons can select and control different surgical characteristics and pulse modes depending on the particular procedure being performed and surgical conditions encountered. User interfaces should include additional controllable display elements that allow different modes and surgical parameters to be quickly and easily adjusted. These improvements should be made without unduly complicating the user interface and how it functions. Further, interfaces should be capable of effectively representing various operating parameters of various ultrasound driving modes, including continuous, linear, pulse, burst, and new modes, which can be combinations and modifications of known modes. Being able to quickly adjust pulse parameters in an understandable manner also simplifies setting up the equipment, reduces operating costs and improves safety.

BRIEF SUMMARY OF THE INVENTION

According to one embodiment of the invention, a user interface for an ocular surgical system, such as phacoemulsification and vitreo-retinal surgical systems, that generates pulses that are adjusted in response to a controller includes a display element and a window that are displayed on a display screen. The display element includes a representation of a parameter of pulses generated by the ocular surgical system relative to a position of the controller. The window is generated and displayed on the display screen in response to touching the display screen. The window includes a display element that includes a representation of the parameter of the pulses relative to the position of the controller.

According to an alternative embodiment of the invention, a user interface for an ocular surgical system, such as phacoemulsification and vitreo-retinal surgical systems, includes a display element and a window that are displayed on the display screen. The display element includes a representation of a parameter of pulses generated by the ocular surgical system relative to a position of the controller. The window is generated in response to touching the display screen. The window includes a display element that has a representation of the parameter of the pulses relative to the position of the controller and an adjustment element for changing a value of the parameter that is represented in the display element in the window. A current representation of the parameter displayed in the window is changed to a different representation of the parameter in response to touching the display screen at the window. A value of the parameter is changed by touching the display screen at the adjustment element. After the user has adjusted the parameter, the window can be closed by touching the display screen at a pre-defined area of the window.

According to another alternative embodiment of the invention, a user interface for an ocular surgical system, such as phacoemulsification and vitreo-retinal surgical systems, includes a display element and a window that are displayed on a display screen of the system. The display element includes a representation of a parameter of the pulses relative to a position of the foot pedal. The window is generated in response to touching the display screen of the system. The window includes a display element having a representation of the parameter of the pulses relative to the position of the controller and an adjustment element for changing a value of the parameter represented in the display element. At least three representations of the parameter are sequentially displayed in the display element in the window by touching the display screen at the display element in the window. This allows a user to scroll through the representations. The representation that is displayed in the display element in the window is the selected representation of the parameter. A value of the parameter is changed by touching the display screen at the adjustment element. After the parameter is adjusted, the window is closed by touching the display screen at a pre-defined area of the window.

According to another alternative embodiment, a user interface for an ocular surgical system, such as phacoemulsification and vitreo-retinal surgical systems, that generates pulses that are adjusted in response to a controller based on settings displayed on a display screen of the ocular surgical system includes a first display element and a window. The first display element is shown on the display screen and that includes a value of a parameter of pulses generated by the ocular surgical system. The window is displayed on the display screen and generated in response to touching the display screen. The window includes a second display element. The second display element includes the value of the parameter of the pulses generated by the ocular surgical system.

According to a further alternative embodiment, a user interface for an ocular surgical system that generates pulses that are adjusted in response to a controller based on settings displayed on a display screen of the ocular surgical system includes a first display element and a window. The first display element is shown on the display screen and includes a value of a parameter of pulses generated by the ocular surgical system. The window is displayed on the display screen and generated in response to touching the display screen at the first display element. The window includes a second display element that includes the value of the parameter of the pulses generated by the ocular surgical system and an adjustment element for changing the value of the parameter.

In various embodiments, a current representation of the parameter displayed in the window is changed to a different representation in response to touching the display screen at the window, e.g., the display element in the window. The window can be generated by touching the display screen at the initial display element. The adjustment element that is used to adjust a parameter can be one or more arrows and slide bars. A pre-defined area of the display screen can bed touched to close the window. The pre-defined area can be a pre-defined area within the window, e.g., defined by an icon or button. The parameter that is represented in the window can be non-ultrasonic and ultrasonic parameters, e.g., power, pulse on-time, and pulse off-time. The parameter in the display element in the initial display screen and in the window can be increasing, decreasing, constant, linear and non-linear, such as exponential or a polynomial.

Further, in various embodiments, the window can be generated in response to touching the display screen at the first display element. A window can include various adjustment elements, e.g., one adjustment element or a pair of adjustment elements. The adjustment elements can be an arrow or a slide bar. Further, the window can include an enable element, such as enable and disable buttons, to select whether a particular feature of the ocular system is operable. The pop-up or dialog window can also be deleted or fade away after a pre-determined amount of time of inactivity. Alternatively, the user can close the window by pressing a button or element in the window, such as a "Done" button. Further, parameter values can be selected from a menu of available values.

BRIEF DESCRIPTION OF THE SEVERAL VIEWS OF THE DRAWINGS

A more complete understanding of embodiments and the advantages thereof may be acquired by referring to the following description, taken in conjunction with the accompanying drawings, in which like reference numbers indicate like features and wherein:

FIG. 6 illustrates exemplary linear and non-linear representations of pulse characteristics or parameters relative to a position of a foot pedal according to one embodiment;

FIG. 7 illustrates exemplary non-linear representations of on-time and off-time that decrease when the foot pedal is pressed;

FIG. 8 illustrates exemplary non-linear representations of on-time and off-time that increase when the foot pedal is pressed;

FIG. 9 illustrates a menu that includes representations of off-time according to one embodiment in which off-time decreases when the foot pedal is pressed;

FIG. 10 illustrates exemplary sequences of displaying horizontal, increasing and decreasing on-time and off-time representations according to one embodiment in which a user can scroll through different representations;

DETAILED DESCRIPTION OF THE INVENTION

Figure 1:
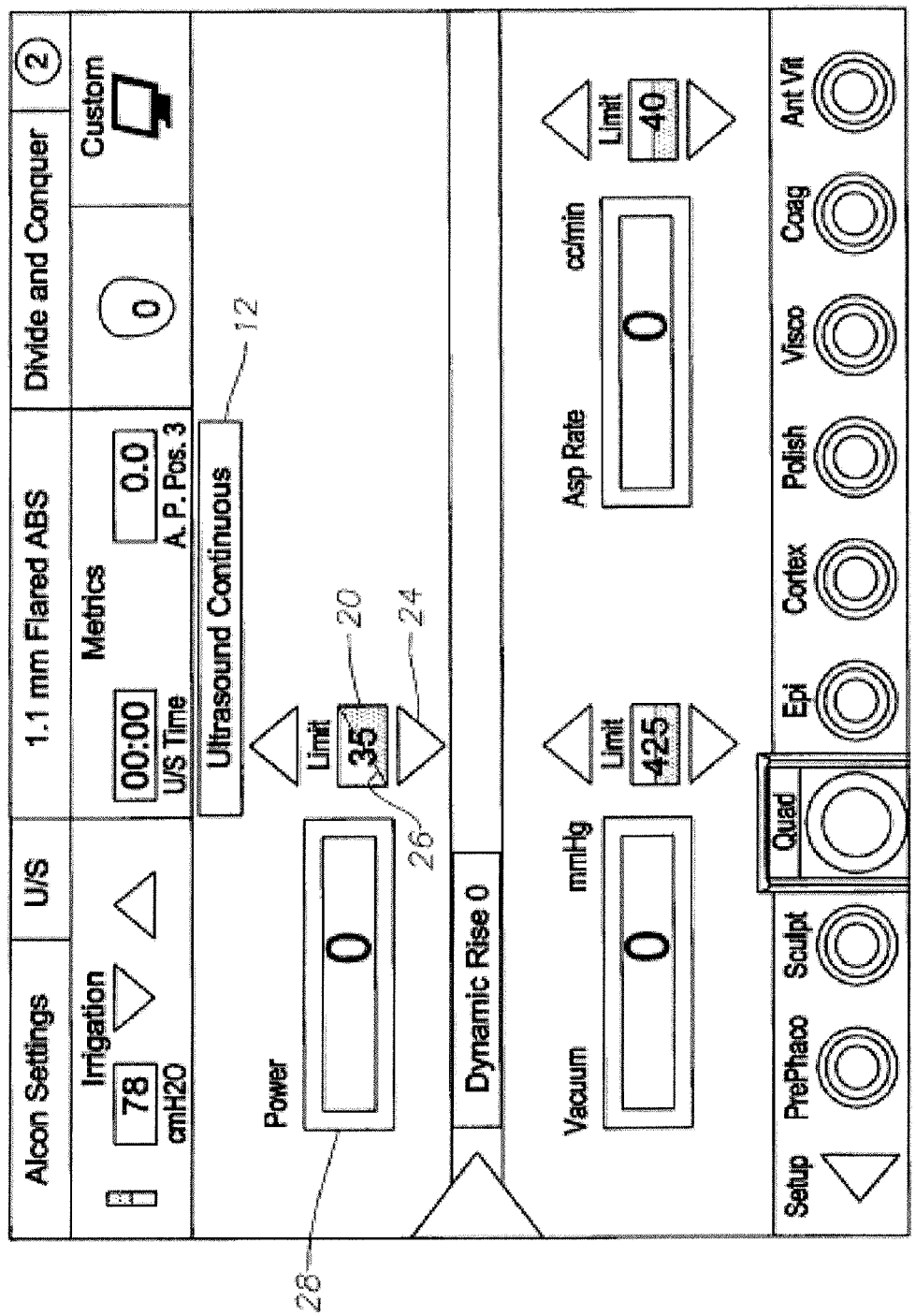
FIG. 1 illustrates a known graphical user interface for use with a phacoemulsification surgical system in "continuous" mode.
Figure 2:
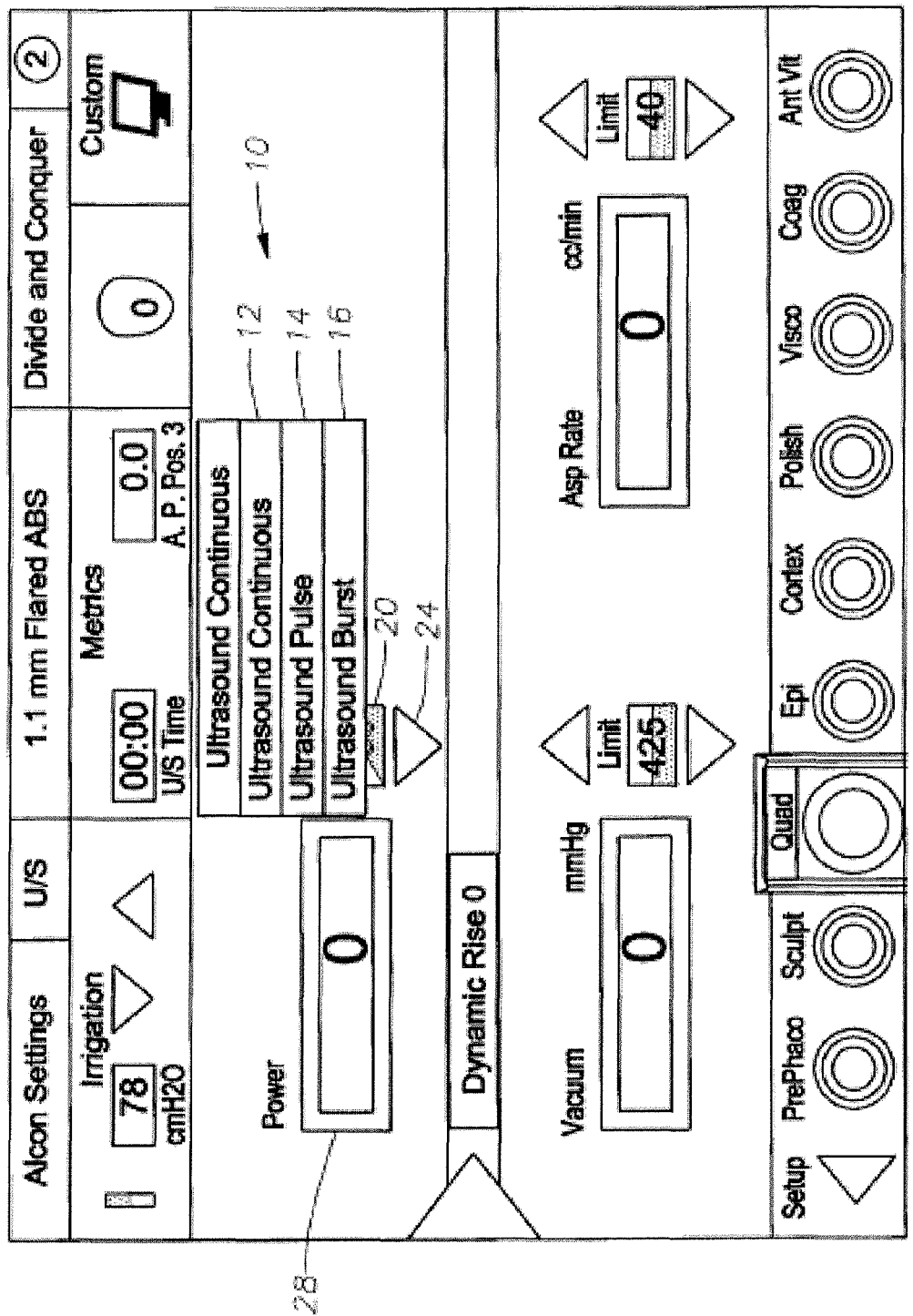
FIG. 2 illustrates the interface shown in FIG. 1 after the "continuous" mode menu bar is selected to generate a drop down menu of available pulse modes.

In the following description, reference is made to the accompanying drawings which form a part hereof, and which show by way of illustration specific embodiments in which the invention may be practiced. It is to be understood that changes may be made without departing from the scope of invention.

Embodiments of the invention are directed to a graphical user interface that provides improved control over the ultrasound driving or pulse modes that are generated by an ocular surgical system, such as a phacoemulsification surgical system, and improved control over the parameters of the different pulse modes. Embodiments provide display elements that can be quickly and easily selected and adjusted by a surgeon to select different modes, while allowing various pulse parameters to be adjusted to customize the various modes. The pulse modes that can be selected include "Continuous," "Pulse" and "Burst" modes and, in addition, hybrid or combination modes that were not previously readily available for use in phacoemulsification systems. Representations of parameters, characteristics and the functions of pulses are displayed in display elements. The representations can be changed by touching a display screen at a particular display element to generate a menu from which a representation of a pulse characteristic, such as the on-time and the off-time, can be selected by the user. Alternatively, a user can scroll through different representations of the characteristics or function of the on-time and the off-time of the pulses. The representation that is selected represents the function or behavior of the pulse characteristic, e.g., whether and how the on-time and the off-time vary in response to displacement of a controller, such as a foot pedal, and the types and characteristics of pulses that are generated by the phacoemulsification system. A separate window can be generated in response to touching the display screen to adjust the representation and/or values.

Embodiments of the invention provide improvements over known interfaces by allowing on-time, off-time and other pulse parameter representations to be adjusted so that they increase linearly, increase non-linearly, decrease linearly, decrease non-linearly, and remain substantially constant relative to displacement of a foot pedal. These settings determine whether the on-time and/or off-time decrease or increase linearly or non-linearly or remain constant. Different pulse modes can be generated by selecting the manner in which the on-time and the off-time vary (or not vary). For example, nine different pulse modes can be selected when the on-time and the off-time each can increase, decrease or remain constant in response to movement of the foot pedal. The power limit, the on-time and the off-time, can be adjusted using up/down arrows and other suitable adjustment mechanisms. Persons skilled in the art will appreciate that embodiments of the invention can be utilized with other surgical equipment including, but not limited to, neurosurgery equipment, where control of various instruments is also performed with a remote foot pedal. For purposes of explanation, not limitation, this specification describes embodiments related to phacoemulsification procedures and their associated operating parameters.

Figure 5:
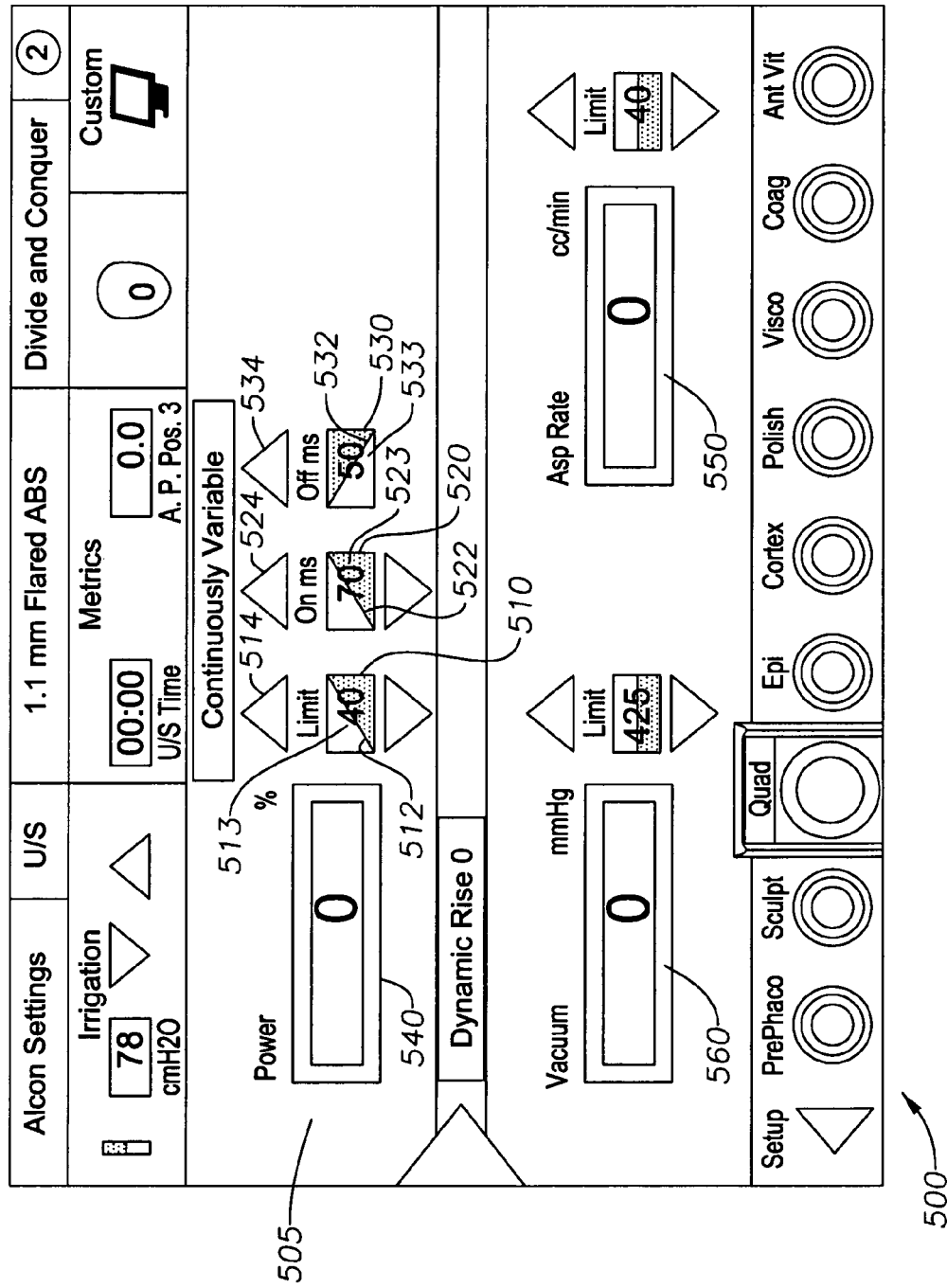
FIG. 5 illustrates a graphical user interface for a phacoemulsification surgical system according to one embodiment of the invention that includes representations of the functions of pulse on-time and off-time.

Referring to FIG. 5, a user interface 500 for an ocular surgical system, such as a phacoemulsification surgical system, according to one embodiment is displayed on a display screen 505 of the system. The interface 500 includes a power display element 510, an on-time display element 520, and an off-time display element 530.

The current power level, as controlled by the foot pedal, is shown in a current power display element 540. In the illustrated embodiment, the display elements 510, 520 and 530 are rectangle-shaped display elements. Indeed, other shapes besides rectangular shapes can be utilized, and rectangle-shaped display elements are provided for purposes of illustration, not limitation. The interface 500 also includes other display elements and adjustments for other phacoemulsification surgical parameters, such as aspiration flow rate (Asp Rate) 550 and vacuum limit pressure (Vacuum) 560, as known in the art. Operation of these other display elements 550 and 560 is not discussed further in this specification. Pressing and releasing the foot pedal controls the operation of the surgical devices according to the corresponding operating parameters and parameter values that are represented in the interface 500 and programmed in the system.

The power display element 510 includes a representation 512 of the behavior or function of power relative to a position of the foot pedal, the on-time display element 520 includes a representation 522 of the behavior or function of the on-time of the pulses relative to a position of the foot pedal, and the off-time display element 530 includes a representation 532 of the behavior or function of the off-time of the pulses relative to a position of the foot pedal. In one exemplary surgical system, the parameter values change when the foot pedal moves, and the parameter values reflect the actual parameter values. When the foot pedal is not depressed, the values that are displayed are the limits of the values that are achieved when the foot pedal fully depressed. Persons skilled in the art will appreciate that other conventions can be used and the described convention is an exemplary convention.

The graphic representations can be easily and quickly selected and adjusted by a surgeon before and during surgery. The display elements 510, 520 and 530 also includes respective power, on-time and off-time limits or values 513, 523 and 533. Although embodiments are described with reference to "Off" or off-time and "On" of on-time, persons skilled in the art will appreciate that other ultrasound parameters, such as pps and duty cycle, and non-ultrasound parameters can be represented in a user interface. For purposes of explanation, not limitation, this specification refers to on-time and off-time parameters. Further, persons skilled in the art will appreciate that different combinations of parameters can be used to represent different types of pulses. For purposes of explanation, this specification refers to on-time and off-time.

Referring to FIG. 6, a representation of a pulse characteristic can have various shapes depending on the desired relationship or function between the pulse parameter and the position of the foot pedal. A representation of a characteristic or parameter of a pulse can be linear or non-linear, to represent a linear or non-linear function of power, on-time and/or off-time. A linear representation can be an increasing linear representation 600, a horizontal or constant linear representation 620, and a decreasing linear representation 610. A non-linear representation can be an increasing non-liner representation 630 and a decreasing non-linear representation 640.

FIG. 7 illustrates exemplary non-linear representations. Non-linear representations 700-750 decrease non-linearly in different manners. Exemplary non-linear representations include exponential and polynomial representations so that the power, on-time and/or off-time varies exponentially or in accordance with a polynomial with movement of the foot pedal. Representations 700-720 and corresponding functions of the power, on-time and/or off-time decrease less rapidly when the foot pedal is initially depressed, and decrease more rapidly as the foot pedal is depressed further. Representations 730-750 and corresponding functions of the power, on-time and/or off-time decrease more rapidly when the foot pedal is initially depressed, and decrease more slowly as the foot pedal is depressed further. FIG. 8 illustrates similar relationships with increasing representations of the behavior or functions of a power, on-time and/or off-time.

For purposes of explanation and illustration, not limitation, this specification refers to linear representations, e.g., increasing linear, constant, and decreasing linear representations and related linear functions of power, on-time and/or off-time. Persons skilled in the art will appreciate that the power, on-time and off-time can be controlled with linear representations, non-linear representations and combinations thereof. Persons skilled in the art will also appreciate that a linear representation may represent a characteristic of a pulse that is substantially linear and that includes some non-linear components in actual practice. For example, the relationship between the actual power and the position of the foot pedal may not be exactly linear due to mapping the foot pedal position to the amount of power that is generated. Thus, there may be some deviations from a truly "linear" representation in practice due to mapping and other factors.

In the embodiments shown in FIG. 6, an increasing linear representation 600 extends from a bottom left corner to a top right corner of a display element to illustrate that the parameter being represented increases linearly as the foot pedal is pressed and decreases linearly as the foot pedal is released. A horizontal or constant linear representation 620 extends between opposite sides of a display element and illustrates that the parameter being represented remains substantially constant at various foot pedal positions. A decreasing linear representation 610 extends from a top left corner to a bottom right corner of a display element and illustrates that the parameter being represented decreases linearly as the foot pedal is pressed and increases linearly as the foot pedal is released. In alternative embodiments, increasing and decreasing linear representations 600 and 610 and corresponding functions of the pulse parameter may extend between a side and a corner of a display element or two sides of a display element, while still showing an increasing or decreasing relationship. This may represent, for example, that the starting value of the pulse parameter, such as the on-time and the off-time, is a non-zero value.

Referring again to FIG. 5, the power limit display element 510 includes a power limit or value 513, the on-time display element 520 includes an on-time limit or value 523 and the off-time display element includes an off-time limit or value 533. The limits are adjusted using respective up/down arrows 514, 524 and 534 or other suitable adjustment mechanisms, such as slide bars (not shown in FIG. 5). This specification refers to up/down arrows for purposes of illustration, not limitation. Initial power, on-time and off-time values, whether minimum or maximum values, can be set or programmed as necessary. For example, the system can be configured so that the minimum power value is 0% or another desired value when the foot pedal is in its home position, e.g., when the foot pedal is released. As a further example, the initial on-time or, alternatively, the minimum on-time, can be 0 ms or a non-zero value. Similarly, the initial off-time or, alternatively, the minimum off-time, can be 0 ms or a non-zero value. Initial values or, alternatively, minimum values, can set using another interface screen or programming the values into the system. Maximum power, on-time and off-time can also be set or programmed as appropriate.

For example, if the on-time is an increasing function (e.g., increasing linear function), then the on-time limit 523 represents the maximum on-time that can be achieved when the foot pedal is fully depressed. The minimum on-time can be zero or another selected value, e.g., 20% of the maximum value. The minimum on-time can be determined using a formula function or other techniques. As a further example, if the on-time function is a decreasing function, then the on-time limit 523 represents the minimum on-time value that can be achieved when the foot pedal is fully depressed. The maximum on-time can be selected as appropriate. Similar controls apply to the power and off-time limits. The following examples illustrate these relationships.

If the maximum value 523 of the on-time is 70 ms and the on-time representation 522 increases linearly, then the on-time increases linearly from zero or a minimum value (e.g., 20% of 70 ms) to 70 ms in a linear manner as the foot pedal is pressed. The minimum on-time or starting point can be set or programmed as needed. As a further example, if the on-time representation 522 decreases linearly, then the on-time decreases from a maximum value to a minimum value of 70 ms in a linear manner as the foot pedal is pressed. The maximum on-time or starting point can be set or programmed as needed.

Similarly, if the off-time limit 533 is 70 ms and the off-time representation 532 increases linearly, then the off-time increases from a minimum value to 70 ms as the foot pedal is pressed. As a further example, if the off-time decreases linearly, then the off-time decreases from a maximum value to a minimum value of 70 ms in a linear manner as the foot pedal is pressed.

If the maximum value of the off-time is 50 ms, and the off-time representation is horizontal, then the off-time remains substantially constant at 50 ms at different foot level positions. If the maximum value of the on-time is 50 ms, and the on-time representation is horizontal, then the on-time remains substantially constant at 50 ms at different foot level positions.

Thus, the limit values 513, 523 and 533 within each of the power, on-time and off-time display elements 510, 520 and 530 represent a maximum or minimum limit of each parameter when the foot pedal is fully depressed depending on whether the parameter increases or decreases when the foot pedal is pressed. The limit value is a maximum value when the parameter increases when the foot pedal is pressed, and is a minimum value when the parameter decreases when the foot pedal is pressed.

In the illustrated embodiment, the values are superimposed over their respective representations. In other words, the representation appears in the background of a display element. For example, the value 513 is superimposed over the power representation 512, the value 523 is superimposed over the on-time representation 522 and the value 533 is superimposed over the off-time representation 532. In alternative embodiments, the representations can also be superimposed over the values depending on display preferences.

A surgeon can select and switch representations and the manner in which the power, on-time and off-time function in different manners. Referring to FIG. 9, according to one embodiment, the surgeon can touch the display screen at a display element so that a menu 900 of different representations is displayed as a drop-down list. The surgeon can then select a new representation or function of the power, on-time and/or off-time from the menu 900. For example, referring to FIGS. 5 and 9, a surgeon can touch the display screen 505 at the off-time display element 530. As a result, a menu 900 of decreasing representations is displayed, and the surgeon can then select one of the representations from the menu 900. The selected representation represents how the pulse characteristic functions. The menu 900 can include different numbers of decreasing, increasing and constant or horizontal representations. FIG. 9 illustrates a menu 900 having decreasing representations for purposes of illustration, not limitation. Each of the power limit, on-time and off-time representations can be adjusted using a menu 900.

Referring to FIG. 10, according to another embodiment, a surgeon can touch the display screen 505 at a display element to change the representation of the pulse characteristic to the desired representation using a scroll menu 1000. Thus, different representations are shown to the surgeon individually rather than shown as a group or menu 900, as shown in FIG. 9. In this embodiment, each time the surgeon touches the display screen 505 at a particular display element, the representation of that pulse parameter changes to a new representation. In other words, the surgeon can scroll through different representations of pulse characteristics by touching the display screen 505 at the corresponding display element.

The representations in a scroll menu can appear to the surgeon in different orders. For example, if the initial representation is a horizontal representation, a first touch (Touch 1) of a display element can change the horizontal representation to a linear increasing representation. The next touch (Touch 2) can change the linear increasing representation to a linear decreasing representation. The next touch (Touch 3) can change the linear increasing representation to the horizontal representation. Each of the power limit, on-time and off-time representations can be adjusted in this manner. FIG. 10 illustrates other sequences in which representations may be displayed to a surgeon in response to the surgeon touching the display screen at a display element. Further, alternative embodiments can include other numbers of representations and thus, other sequences of representations that are displayed.

Different ultrasound driving or pulse modes can be generated by the phacoemulsification system by selecting representations of the function or behavior of the power, on-time and off-time, using a menu shown in FIG. 9 or a scrolling menu shown in FIG. 10.

Figure 11:
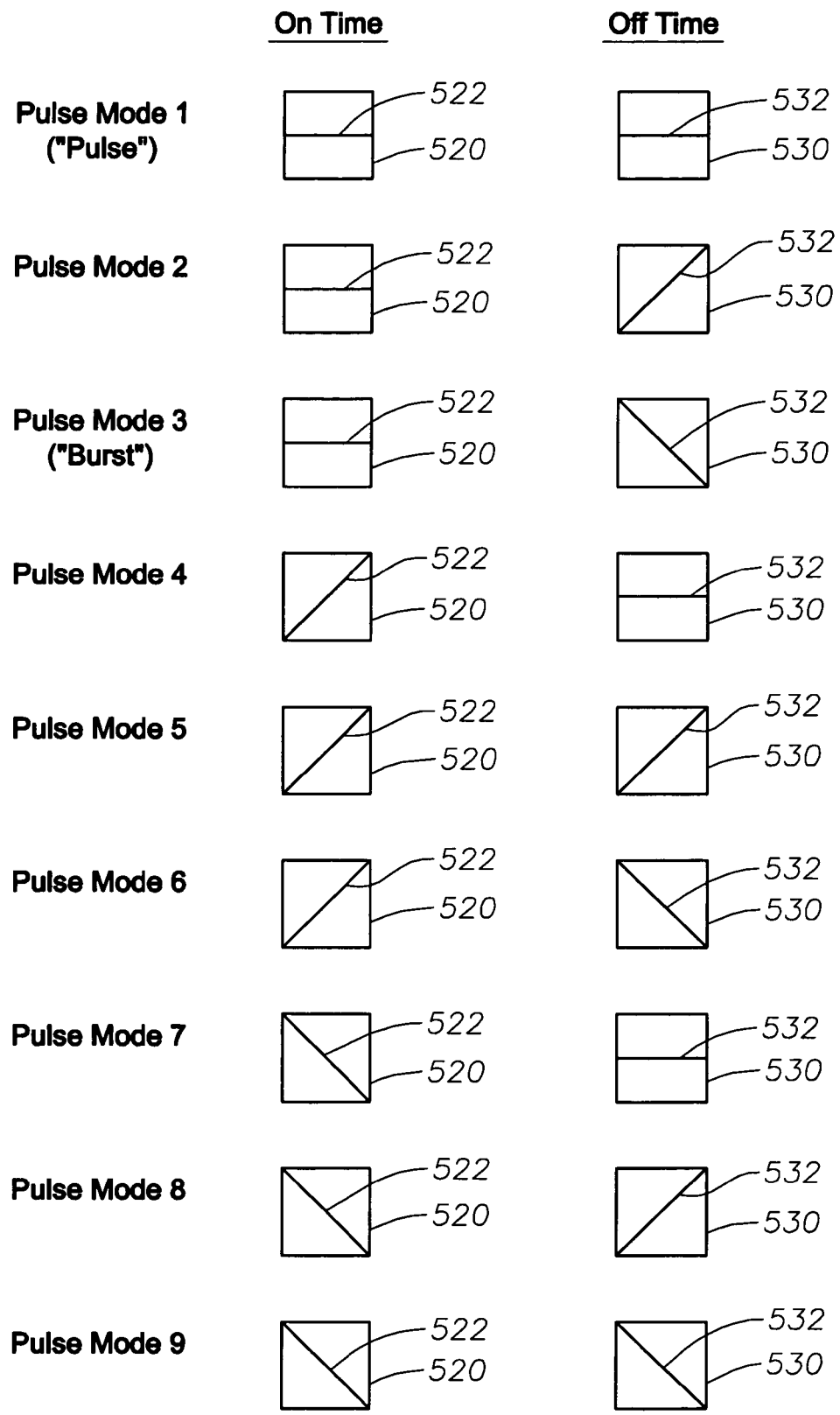
FIG. 11 illustrates nine different pulse modes that can be implemented by selecting one of three on-time representations and one of three off-time representations according to one embodiment.

According to one embodiment, the on-time and the off-time can each be assigned three different representations: linear increasing, linear horizontal or constant, and linear decreasing. Referring to FIG. 11, the total number of possible modes can be determined by multiplying the number of on-time representations and the number of off-time representations. In this embodiment, a surgeon can program nine different pulse modes. Indeed, the number of modes can change when using different numbers of representations.

In Mode 1, both the on-time and the off-time remain substantially constant when the foot pedal is pressed due to the horizontal representations. In Mode 2, the on-time remains substantially constant and the off-time increases linearly in response to the foot pedal being pressed. In Mode 3, the on-time remains substantially constant and the off-time decreases linearly in response to pressing the foot pedal. In Mode 4, the on-time increases linearly and the off-time remains substantially constant in response to pressing the foot pedal. In Mode 5, both the on-time and the off-time increase linearly as the foot pedal is pressed. In Mode 6, the on-time increases linearly and the off-time decreases linearly in response to the foot pedal being pressed. In Mode 7, the on-time decreases linearly and the off-time remains substantially constant in response to pressing the foot pedal. In Mode 8, the on-time decreases linearly and the off-time increases linearly in response to the foot pedal being pressed. In Mode 9, both the on-time and the off-time decrease linearly as the foot pedal is pressed. A surgeon can select one of the nine modes depending on the particular application according to one embodiment. FIGS. 12-19 illustrate exemplary implementations of selected modes. Persons skilled in the art will appreciate that the values provided in FIGS. 12-19 are exemplary values. Indeed, other power, on-time and off-time values may be used as necessary. Accordingly, the values are provided for purposes of explanation, not limitation.

Figure 3:
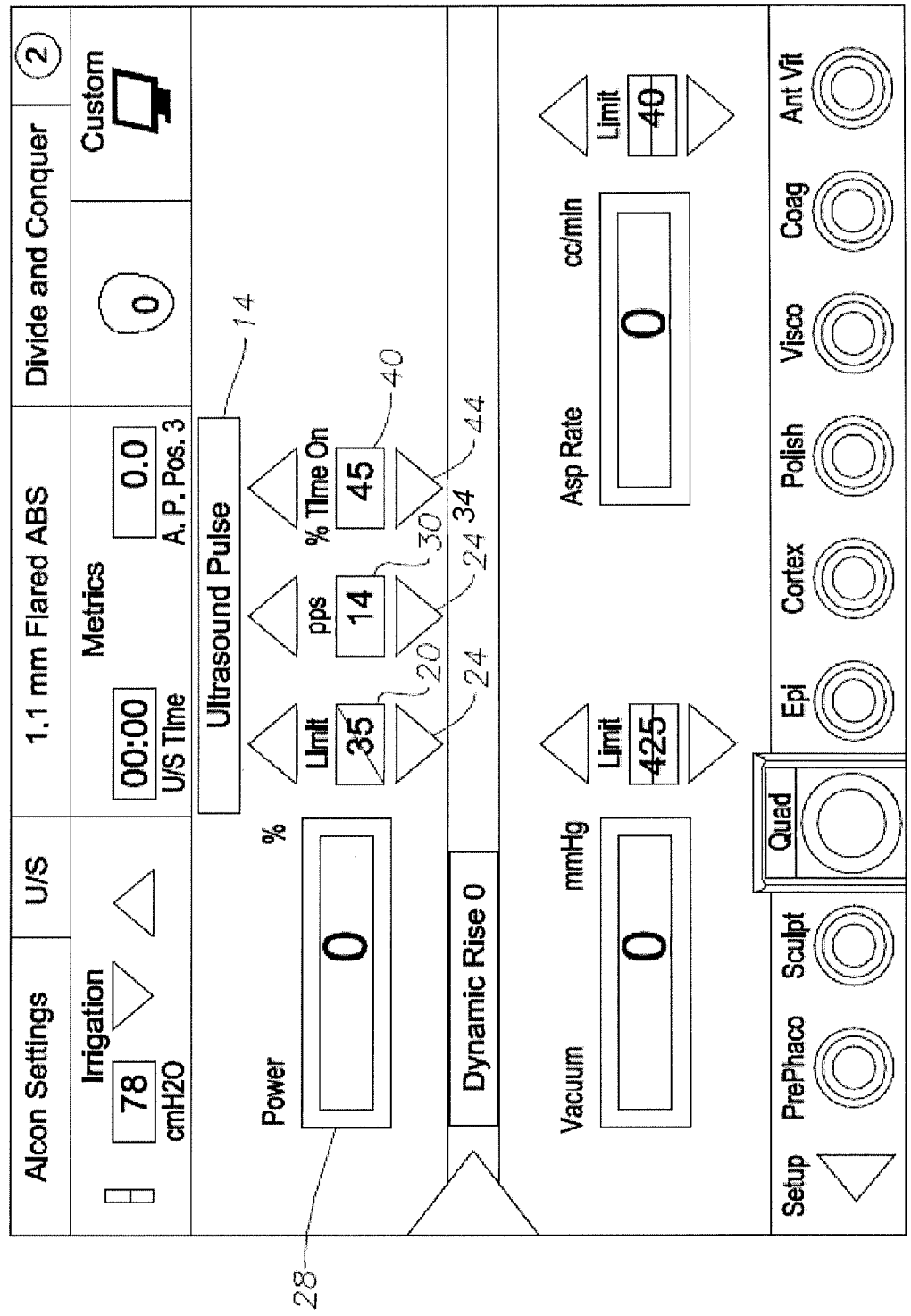
FIG. 3 illustrates the interface shown in FIG. 2 after the "Ultrasound Pulse" menu bar is selected from the menu.
Figure 4:
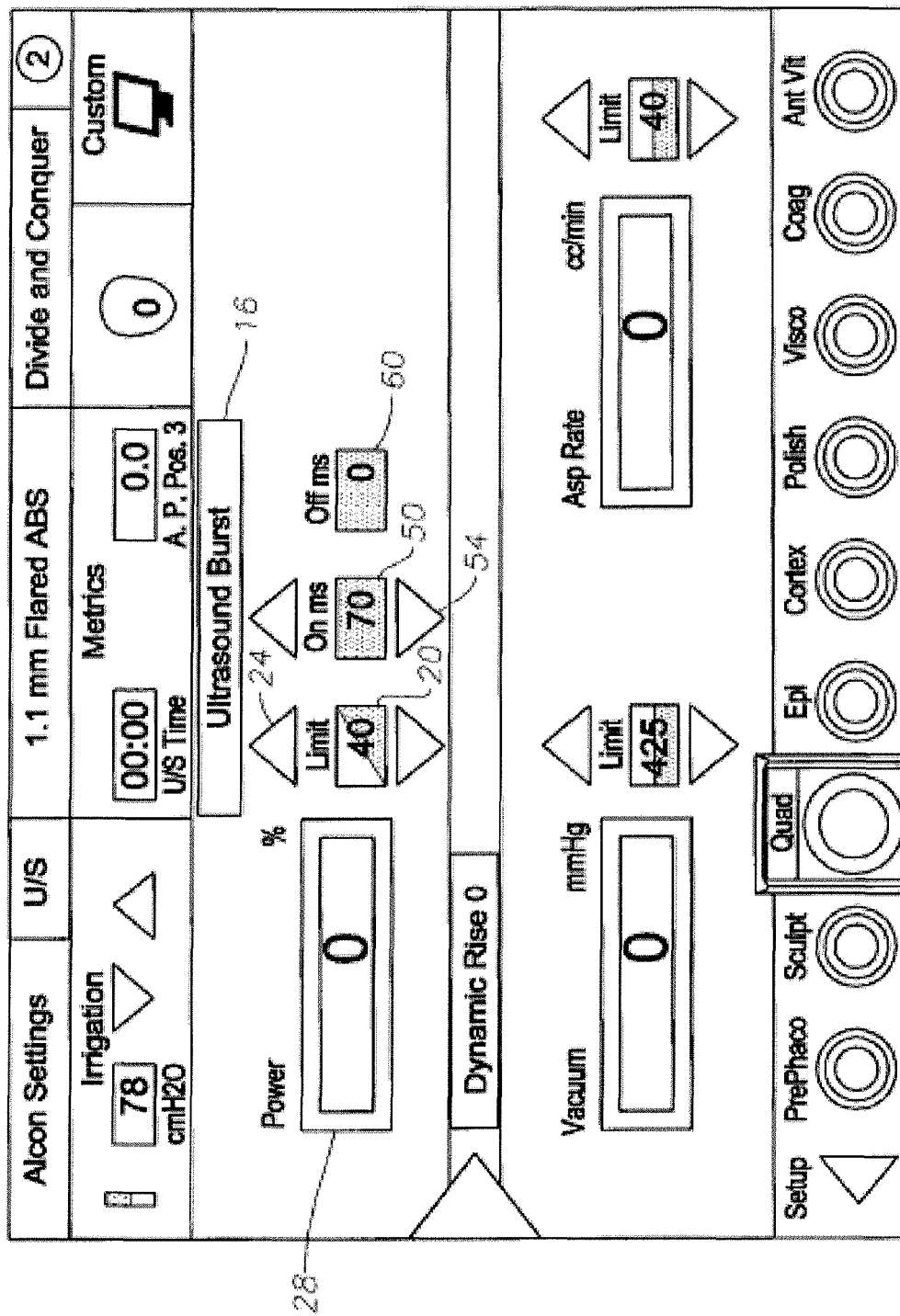
FIG. 4 illustrates the interface shown in FIG. 2 after the "Ultrasound Burst" menu bar is selected from the menu.
Figure 12:
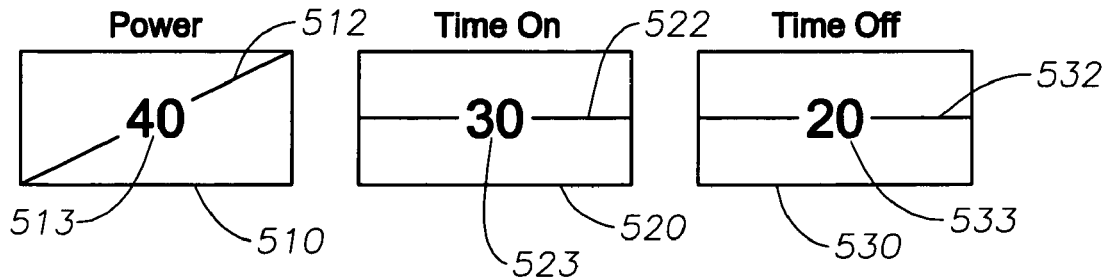
FIG. 12 illustrates an interface for a phacoemulsification surgical system according to one embodiment that is set for "pulse" mode by selecting a constant on-time and a constant off-time.

FIG. 12 illustrates an exemplary implementation of Mode 1, which is commonly referred to as "Pulse" mode. In "Pulse" mode, phacoemulsification power is provided in periodic pulses at a constant duty cycle. The surgeon can increase or decrease the amount of power by pressing or releasing the foot pedal, which increases or decreases the amplitude of the fixed-width pulses. In known interfaces, such as the interface shown in FIG. 3, "Pulse" mode is typically set using the pulse rate expressed in pulses per second (pps) and the duty cycle or on-time, which is expressed in % time on. Embodiments of the invention use on-time and off-time to represent pulses in "Pulse" mode. In the illustrated example, power increases from an initial or minimum value to a maximum value of 40% as the foot pedal is depressed. The on-time remains fixed at 30 ms and the off-time remains fixed at 20 ms throughout different foot pedal positions. Thus, power is adjusted by adjusting the amplitude of fixed-width or constant duty cycle pulses.

Figure 13:
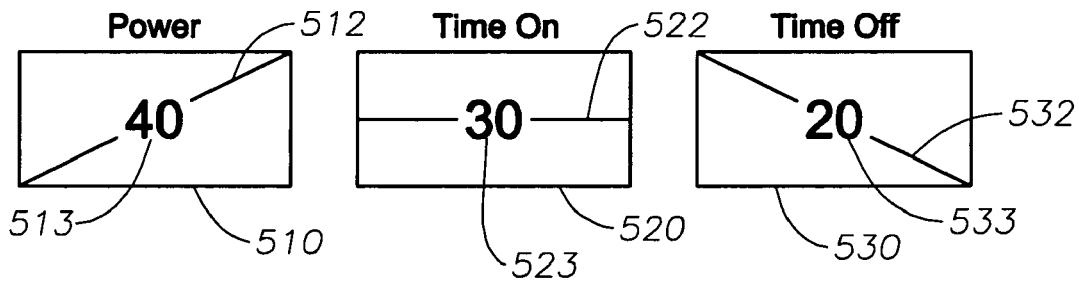
FIG. 13 illustrates an interface for a phacoemulsification surgical system according to one embodiment that is set for a "burst" mode by selecting a constant on-time and a decreasing off-time relative to foot pedal displacement.

FIG. 13 illustrates an exemplary implementation of Mode 3, which is commonly referred to as "Burst" mode. In "Burst" mode, power is provided through a series of periodic, constant amplitude pulses. Each pulse is followed by an "off" time. The off-time is varied by pressing the foot pedal to adjust the amount of power that is delivered to the handpiece. In an alternative burst mode, the amplitude of the pulses may also increase. In the illustrated example, the power increases linearly from an initial or minimum value to a maximum value of 40%. The on-time is fixed or constant throughout different foot pedal positions, and the off-time decreases linearly from an initial or maximum value to a minimum value of 20 ms. For Burst mode, the initial value can be programmed or set to 2500 ms. Indeed, other initial values can also be used depending on the particular application.

Figure 14:
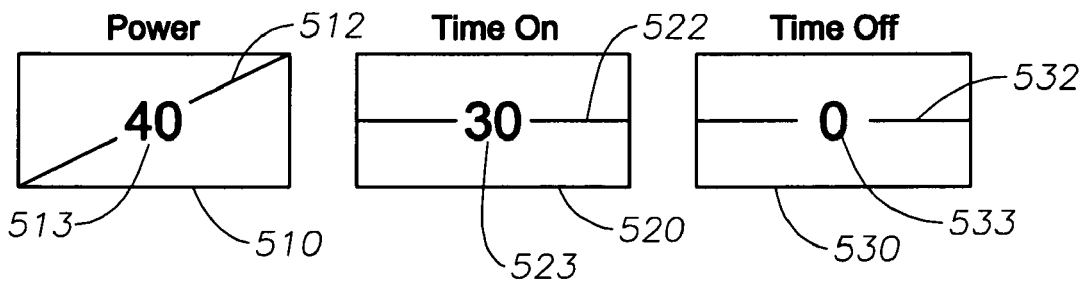
FIG. 14 illustrates an interface for a phacoemulsification surgical system according to one embodiment that is set for "continuous" mode in which the off-time is set to zero.

FIG. 14 illustrates an exemplary implementation of "Continuous" mode. A continuous mode can be selected by setting the off-time to zero when in "Pulse" mode (FIG. 12) or other modes besides "Burst" mode (FIG. 13). Ultrasound power is applied continuously in "Continuous" mode and in a linear manner so that the power increases linearly from zero to 40 as the foot pedal is pressed.

Figure 15:
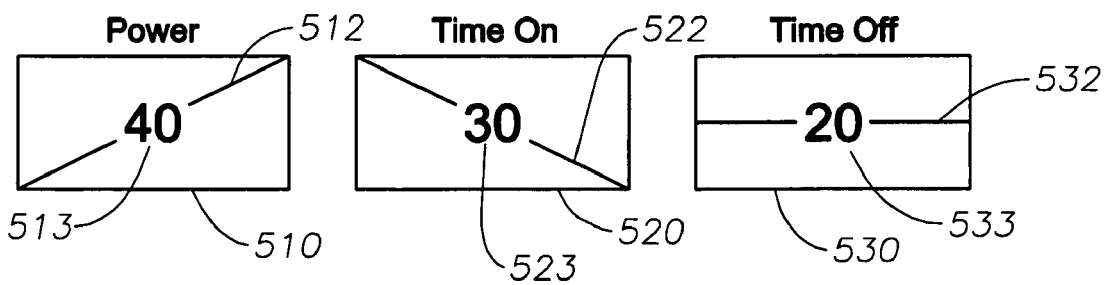
FIG. 15 illustrates an interface for a phacoemulsification surgical system according to one embodiment that is set for a mode in which on-time decreases and the off-time remains constant relative to foot pedal displacement.

FIG. 15 illustrates a mode in which the on-time decreases linearly and the off-time remains constant as the foot pedal is pressed. More particularly, this combination results in power increasing linearly from an initial or minimum value to a maximum value of 40%. The on-time decreases linearly from an initial or maximum value, such as 150 ms to a minimum or ending value of 30 ms in a linear manner. The initial value can be, for example, about a factor of five times the ending value. Thus, in this example, the initial value of 150 ms is five times the ending value of 30 ms. The off-time remains fixed at 20 ms throughout different foot pedal positions.

The mode generated by the settings shown in FIG. 15 can be beneficial since the pulses that are generated by the system can be "adaptive" to various lens hardnesses. For example, when the surgeon sees that a given foot pedal depression does not result in sufficiently rapid progress in lens removal, the surgeon will typically command deeper foot pedal penetration, thus resulting in greater power. Usually, greater power will result in increased repulsion, however, repulsion can be reduced, minimized or eliminated since the duration of the ultrasound pulse with this particular setting will be shortened. This result can be particularly useful when a surgeon is attempting to extract extremely mature cataracts, which are more prone to repulsion at higher powers due to their hardness.

Figure 16:
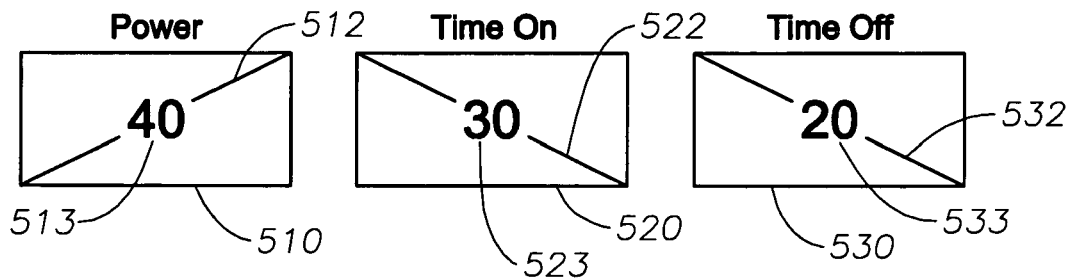
FIG. 16 illustrates an interface for a phacoemulsification surgical system according to one embodiment that is set for a mode in which both the on-time and the off-time decrease relative to foot pedal displacement.

FIG. 16 illustrates a mode in which the power of pulses increases linearly from an initial or minimum value to a maximum value of 40%. The on-time decreases linearly from an initial or maximum value to a minimum or ending value of 30 ms. As previously discussed, the initial or maximum value can be about a factor of five times the ending value. Thus, in this example, the initial or maximum value can be 150 ms. The off-time decreases linearly from an initial or maximum value, such as 2500 ms, to a minimum or ending value of 20 ms.

Figure 17:
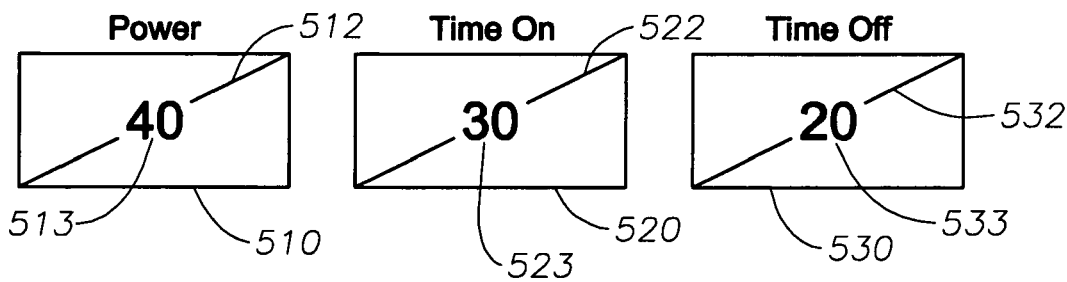
FIG. 17 illustrates an interface for a phacoemulsification surgical system according to one embodiment that is set for a mode in which both the on-time and the off-time increase relative to foot pedal displacement.

FIG. 17 illustrates a mode in which the power, on-time and off-time all increase linearly as the foot pedal is pressed. In the illustrated example, the power increases linearly from an initial or minimum value to a maximum or ending value of 40%. The on-time increases linearly from an initial or minimum value, e.g., 6 ms to 20 ms, to a maximum or ending value of 30 ms. The off-time increases linearly from an initial or minimum value, e.g. 4 ms, to a maximum or ending value of 20 ms.

Figure 18:
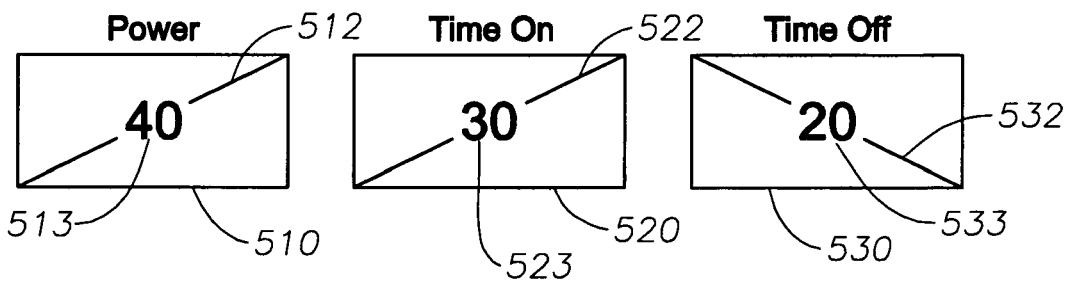
FIG. 18 illustrates an interface for a phacoemulsification surgical system according to one embodiment that is set for a mode in which the on-time increases and the off-time decreases relative to foot pedal displacement.

FIG. 18 illustrates a mode in which the power and on-time increase linearly and the off-time decreases linearly. The power increases linearly from an initial or minimum value to a maximum or ending value of 40%. The on-time increases linearly from an initial or minimum value, e.g., 6 ms, to a maximum or ending value of 30 ms. The off-time decreases linearly from an initial or maximum value, e.g., 2500 ms, to a minimum or ending value of 20 ms. Another exemplary implementation of this mode is shown in FIG. 5.

Figure 19:
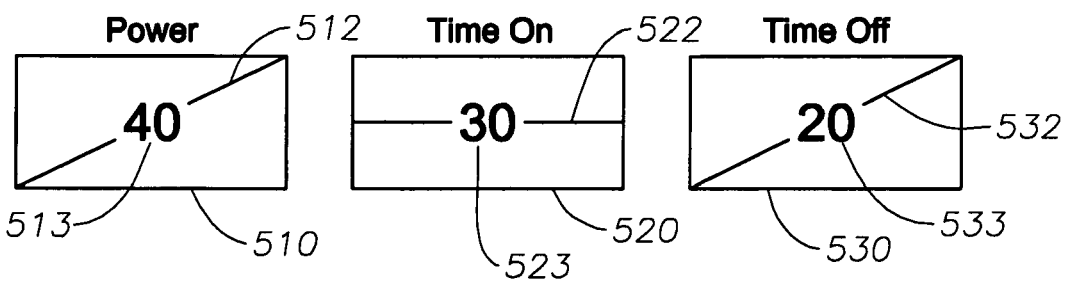
FIG. 19 illustrates an interface for a phacoemulsification surgical system according to one embodiment that is set for a mode in which the on-time remains constant and the off-time increases relative to foot pedal displacement.

FIG. 19 illustrates a mode in which the power increases linearly from an initial or minimum value to a maximum or ending value of 40%. The on-time remains constant at 30 ms throughout different foot pedal positions. The off-time increases linearly from an initial or minimum value, e.g., 4 ms, to a maximum or ending value of 20 ms as the foot pedal is pressed.

Figure 20:
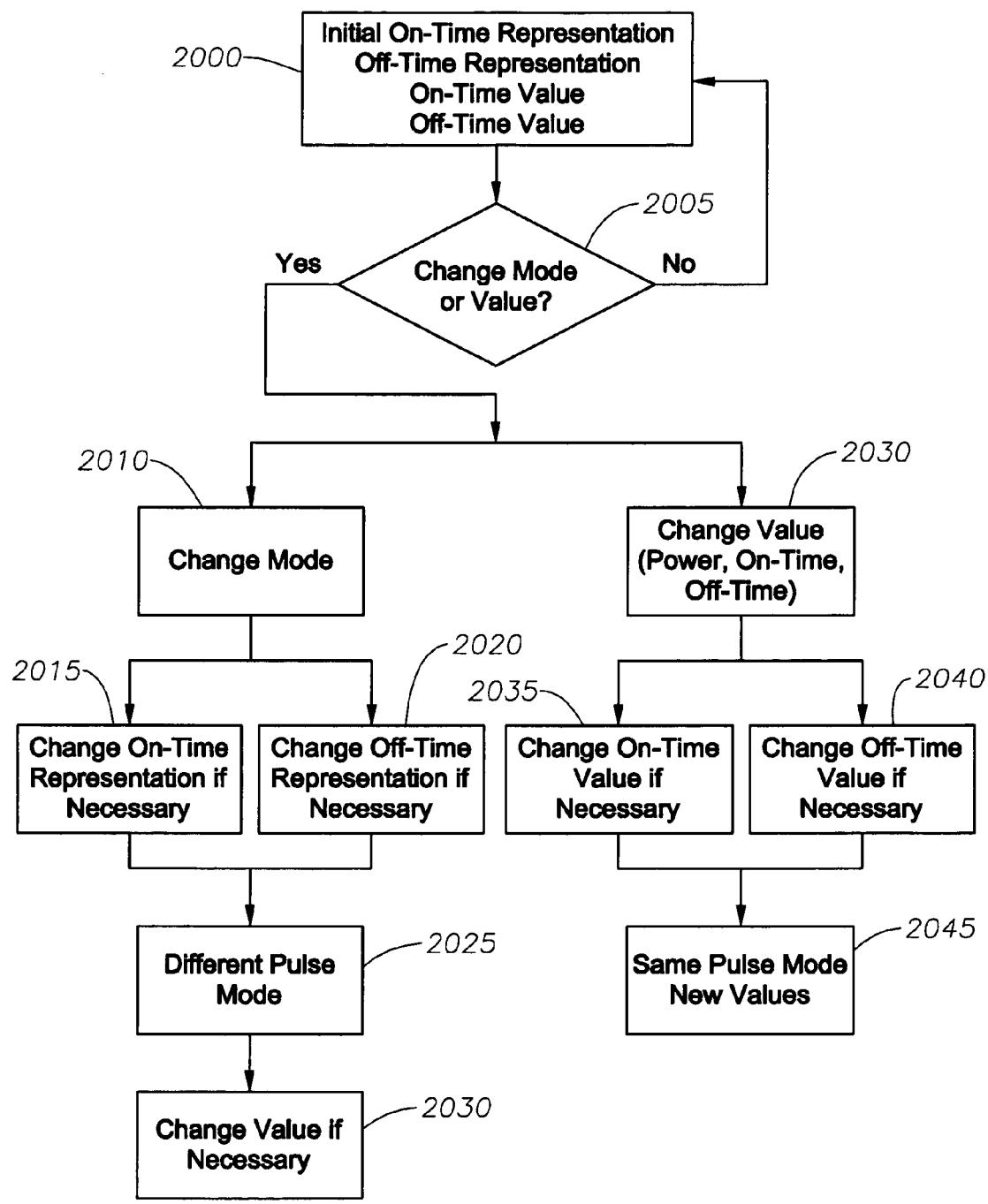
FIG. 20 is a flow chart illustrating a method for selecting a mode and related on-time and off-time values according to one embodiment.

FIG. 20 illustrates a method in which representations and on-time and off-time values can be adjusted. In step 2000, the phacoemulsification surgery system is configured to have an initial on-time representation, an initial off-time representation, an initial on-time value, and an initial off-time value. In step 2005, a decision is made whether the pulse mode or a value of a pulse parameter are to be changed. If not, the initial settings are maintained.

If the pulse mode is to be changed, in step 2010, then the on-time and off-time representations are changed as necessary in steps 2015 and 2020. For example, the surgeon can touch the display screen at an on-time display element to change the on-time representation to one of an increasing linear, constant or decreasing linear representation. Similarly, the surgeon can touch the display screen at an off-time display element to change the off-time representation to one of an increasing linear, constant or decreasing linear representation. The selected combination of the on-time and off-time functions results in one of pulse modes shown in FIG. 11 being selected in step 2025. Of course, different numbers of representations can allow a surgeon to generate different number of pulse modes.

The values of the on-time and off-time parameters can be adjusted in step 2030. More specifically, the on-time value and the off-time value can be adjusted as necessary in steps 2035 and 2040. Thus, the values of the pulse mode are adjusted in step 2045 as necessary.

Figure 21:
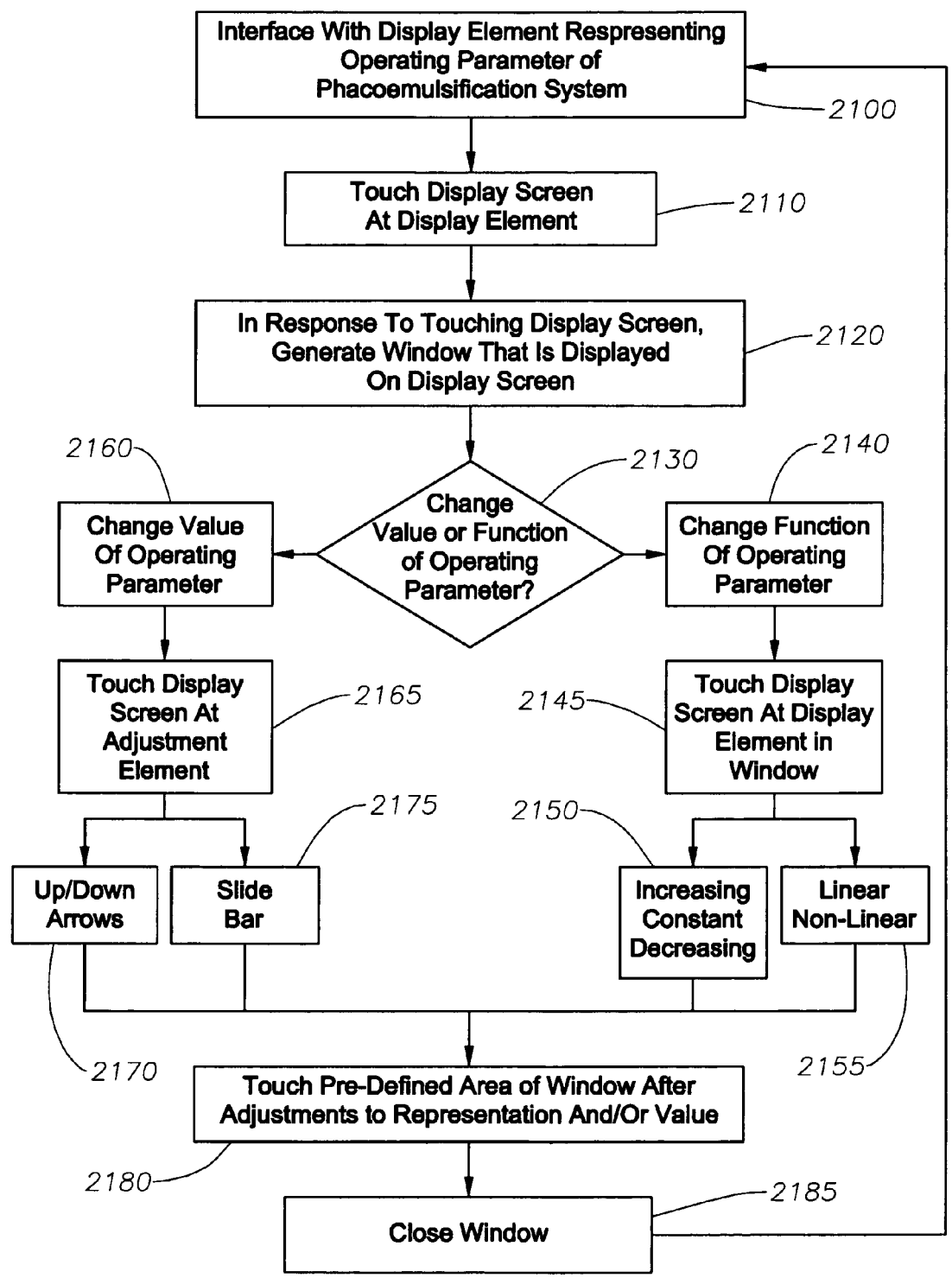
FIG. 21 is a flow chart illustrating a method for adjusting a parameter of a phacoemulsification system by generating a separate display window that is displayed on the display screen.
Figure 22:
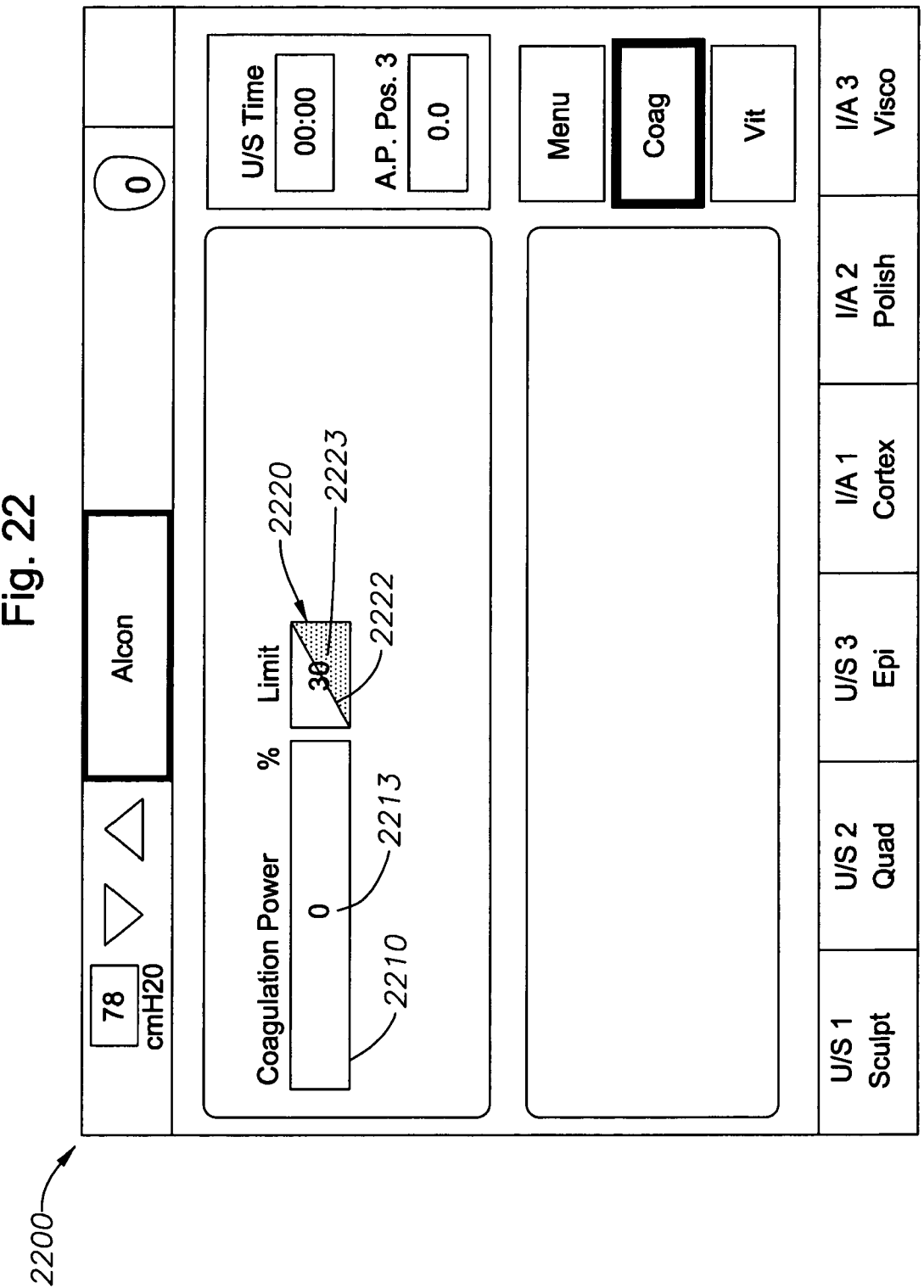
FIG. 22 illustrates an interface screen for use with a phacoemulsification surgical system that shows a continuous surgical parameter value and a representation of the function of the parameter.

FIG. 21 illustrates a method of adjusting values and representations of parameters according to one embodiment. In step 2100, an interface or interface screen is generated. The interface includes a display element that represents a parameter, such as on-time and off-time (or a non-ultrasound parameter) of the phacoemulsification surgery system. In step 2110, a user touches the screen of the display, e.g., at a display element or another pre-defined area. In step 2120, a window is generated in response to touching the display screen. The window enables the user to adjust the representation of the function of the parameter or the value of the parameter in step 2130.

Steps 2140-2155 illustrate changing a representation of the function of the parameter. In step 2145, the user touches the display screen at the display element to adjust the representation. The adjustment can be to make the representation increasing, constant or decreasing in step 2150 and/or to change the representation to linear or non-linear.

Steps 2160-2175 illustrate changing a value of the parameter. In step 2165, the user touches the display screen at the display element to adjust the value. The adjustment can be made using arrows, such as up/down arrows in step 2170 and/or using a slide bar in step 2175. If both the representation and limit value are to be adjusted, the representation can be adjusted first, and then the value. Alternatively, the limit value can be adjusted first and then the representation.

In step 2180, after the representation and/or value of the parameter has been adjusted, the window can be closed touching the display screen at a pre-defined area of the window. In step 2185, the window is closed and the interface includes an updated display element. Further adjustments can be made in a similar manner if necessary.

Referring to FIGS. 22-30, other pop-up or dialog window configurations can be utilized with alternative embodiments. The windows can be generated in a similar manner as described above. Further, as described above, the windows can be used to adjust various ultrasonic and non-ultrasonic parameters, including amplitude, vacuum, irrigation, sensitivity, pulse rate, pulse on-time, pulse off-time, coagulation and threshold.

FIGS. 22-30 illustrate an alternative embodiment of the invention in which a window can be generated in response to touching the display screen of an ocular surgical system to enable a user to change pulse modes, adjust the value of a parameter and/or the function or representation of the parameter. The embodiments shown in FIGS. 22-30 can be used separately from or in conjunction with the embodiments described and shown in FIGS. 5-21. The windows can be used to adjust various aspects ultrasonic an non-ultrasonic parameters of an ocular surgical system, including amplitude, sensitivity, pulse rate, vacuum, irrigation, pulse on-time, pulse off-time, coagulation and threshold. For example, referring to FIG. 22, an exemplary user interface screen 2200 for an ocular surgical system includes a field 2210 and a display element 2220. The display element 2220 includes a representation 2222 of, for example, a non-ultrasound parameter such as coagulation power, and a maximum or minimum value or limit 2223 of the parameter. In the illustrated embodiment, the value is a maximum value since the representation indicates that the power increases as a foot pedal is pressed or another controller is actuated. The current value 2213 of the parameter, expressed as a percentage of the limit 2223, is indicated in the field 2210.

The display element 2220 includes a representation 2222 of the behavior or function of the parameter relative to a position of a controller, such as the foot pedal. A representation 2222 of a parameter can have various shapes depending on the desired relationship or function between the parameter and the position of the foot pedal. For example, the representation 2222 can be linear or non-linear (e.g., exponential or polynomial). The display element 2220 is similar to the display element describe above. Accordingly, additional details concerning the display element 2220 are not repeated. Further, for purposes of explanation and illustration, not limitation, this specification refers to linear representations, e.g., increasing linear, constant, and decreasing linear representations and related linear functions of power. Persons skilled in the art will appreciate that other parameters, such as on-time and off-time, can be controlled, and that parameters can be controlled with linear representations, non-linear representations and combinations thereof.

Figure 23:
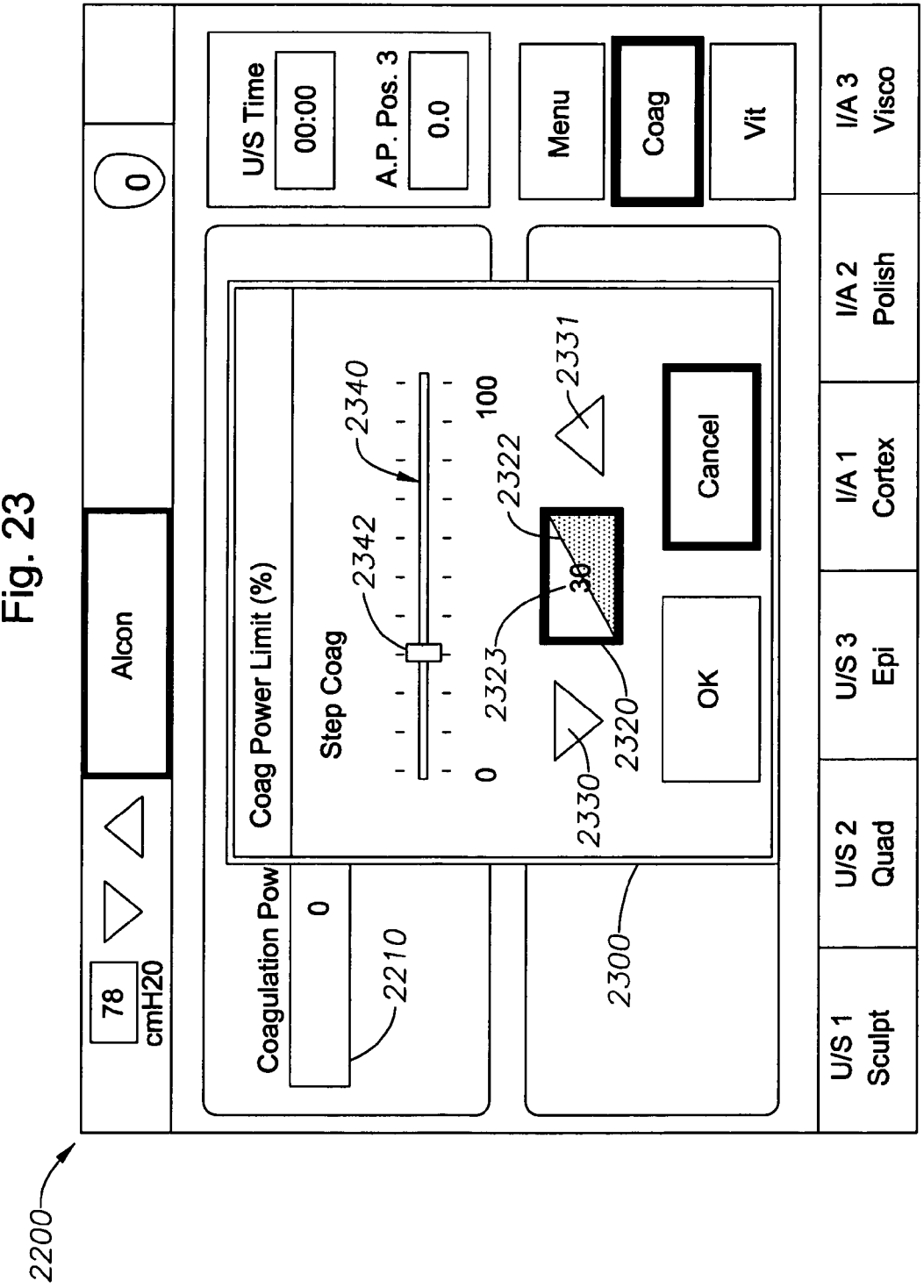
FIG. 23 illustrates an alternative embodiment of the invention in which a separate display or dialog window is generated on the display screen of an ocular surgical system in response to touching the screen.

Referring to FIG. 23, according to one embodiment a pop-up or dialog window 2300 is displayed over the initial display screen 2200 in response to a user touching the display screen, e.g., at or around the display element 2220. The window 2300 includes a display element 2320 having a representation 2322, which is the same as the representation 2222 of the display element 2220 on the initial display screen 2200 behind the window 2300. The window 2300 also includes a maximum value or limit 2323, which is the same as the value 2223 in the display screen 2200 behind the window 2300. The window 2300 can be various shapes and sizes. In the illustrated embodiment, the window 2300 is square and covers a portion of the initial display 2200.

The window 2300 also includes one or more adjustment elements, such as arrows, e.g., up/down arrows 2330 and 2331 (generally 2330) and a slide bar 2340. The window 2300 can include one arrow, multiple arrows, a slide bar and a combination thereof.

Figure 24:
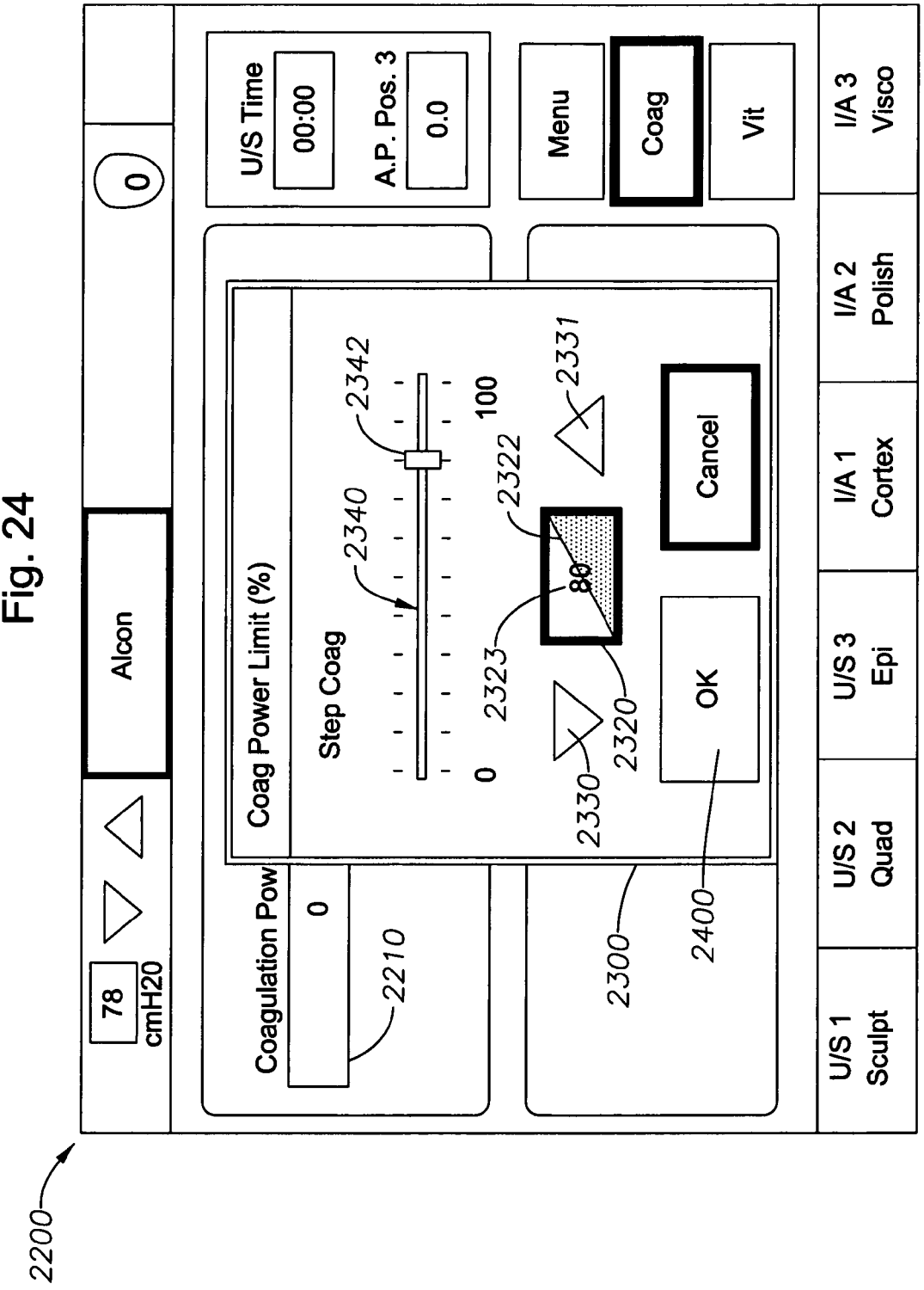
FIG. 24 illustrates adjusting a value of a parameter using an arrow or a slide bar in the window.
Figure 25:
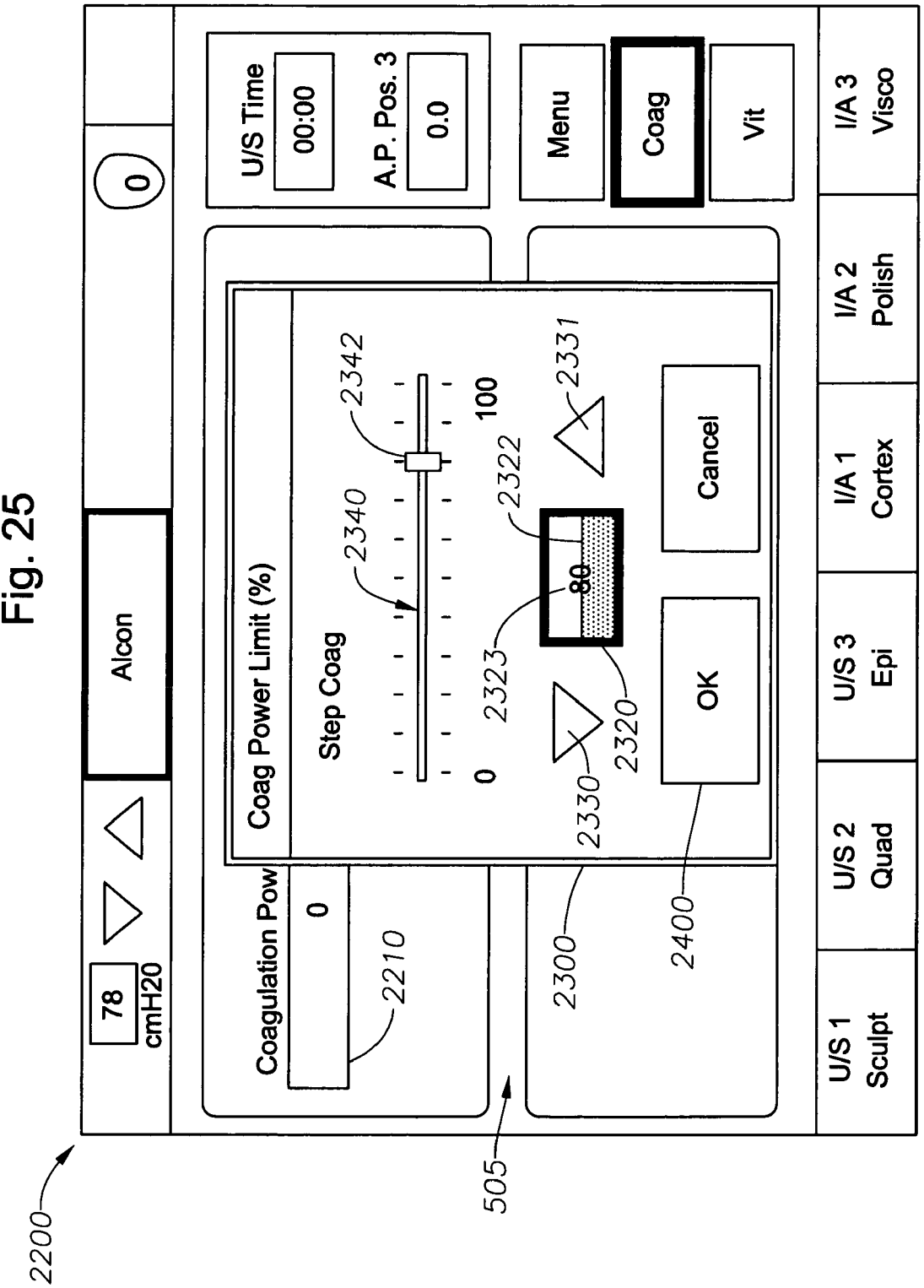
FIG. 25 illustrates adjusting a representation of the function of the parameter by touching the window.

Referring to FIG. 24, a user can touch an arrow 2330 or move a marker 2342 of the slide bar 2340 to adjust the value up or down. For example, as shown in FIGS. 23 and 24, the value is adjusted from 30 to 80 by pressing the up arrow 2331 or moving the marker 2342 to the right. Referring to FIG. 25, the representation of the function of the parameter can also be adjusted by touching the display screen 505 at the display element 2320 in the window 2300. Touching the display element 2320 in the window 2300 changes a current representation of the parameter to a different representation. For example, as shown in FIG. 10, a user can scroll through the different available representations by touching the display element in the window. Alternatively, a menu or pick list can be displayed, e.g., as shown in FIG. 9.

Referring to FIGS. 24 and 25, after the representation and/or value of the parameter has been adjusted, the window can be closed by touching the display screen at a pre-defined area 2400 of the window. For example, in the illustrated embodiment, the pre-defined area 2400 can be an "OK" box or button or another area in the window.

Referring to FIGS. 26-30, other pop-up or dialog window configurations can be utilized with other alternative embodiments. The windows can be generated in a similar manner as described above. Further, as described above, the windows can be used to adjust various ultrasonic and non-ultrasonic parameters, including amplitude, vacuum, irrigation, sensitivity, pulse rate, pulse on-time, pulse off-time, coagulation and threshold for different ocular surgical procedures. For purposes of illustration and explanation, FIGS. 26-30 refer to vitreo-retinal surgical procedures.

Figure 26:
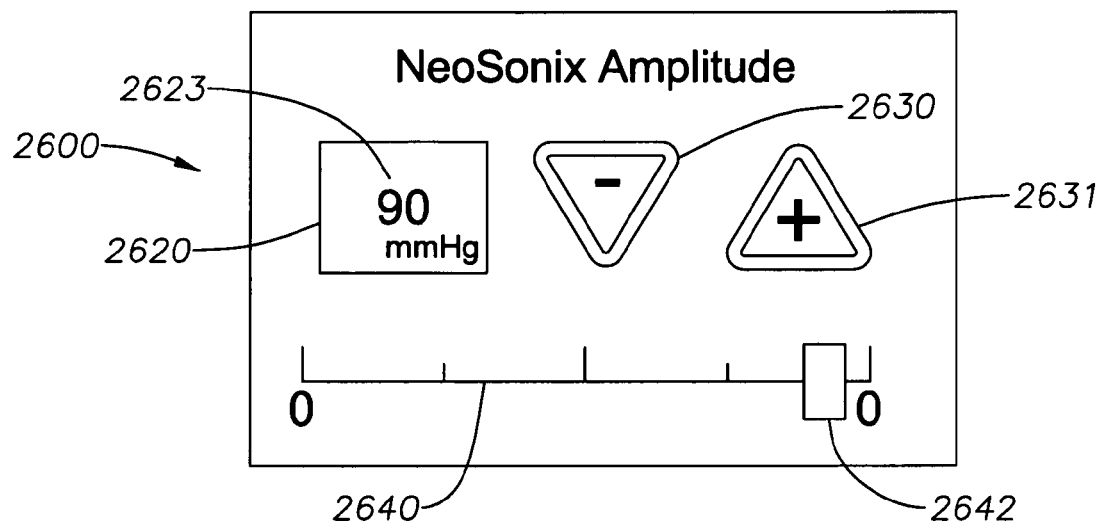
FIG. 26 illustrates an alternative embodiment of a separate display window that is generated by touching a display screen of a phacoemulsification surgical system.

Referring to FIG. 26, a pop-up or dialog window 2600 for a vitreo-retinal surgical system can include a display element 2620 and one or more adjustment elements, e.g., up/down arrows 2630 and 2631. The value 2623 of the parameter in the display element 2620 changes when the user presses the up/down arrows 2630 and 2631. The parameter can also be adjusted by moving a marker 2642 of the slide bar 2640 to adjust the value of the parameter. The values of the parameters can be changed as the user makes the adjustments using the arrows or slide bar. The pop-up or dialog window can fade away or disappear after a pre-determined amount of time of inactivity, e.g., after a pre-determined amount of time after the last touch of the screen. For purposes of illustration and explanation, not limitation, FIG. 26 illustrates adjustments of vacuum or aspiration levels.

Figure 27:
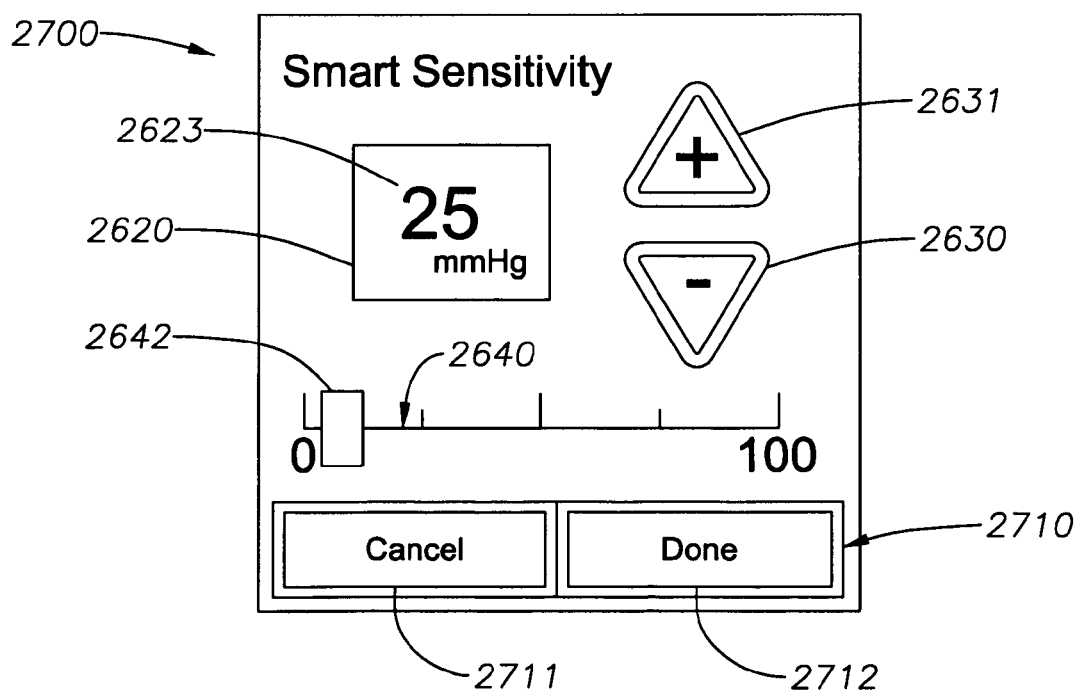
FIG. 27 illustrates another window embodiment that includes an alternative arrangement of components and a selection element that indicates the adjustment is completed.

Referring to FIG. 27, a pop-up or dialog window 2700 can also include a selection element 2710 that indicates the adjustment is completed. For example, the selection element 2710 can be "Cancel" and "Done" buttons 2711 and 2712. The user can close the window after pressing the "Done" button 2712. The "Cancel" button can be pressed if further adjustments are necessary or if the adjustments are incorrect. Thus, with windows that include Done and Cancel buttons, the values of the parameters are changed after the user confirms that the parameter changes can be implemented by pressing the "Done" button, after which the pop-up window or dialog box disappears from the display screen.

Figure 28:
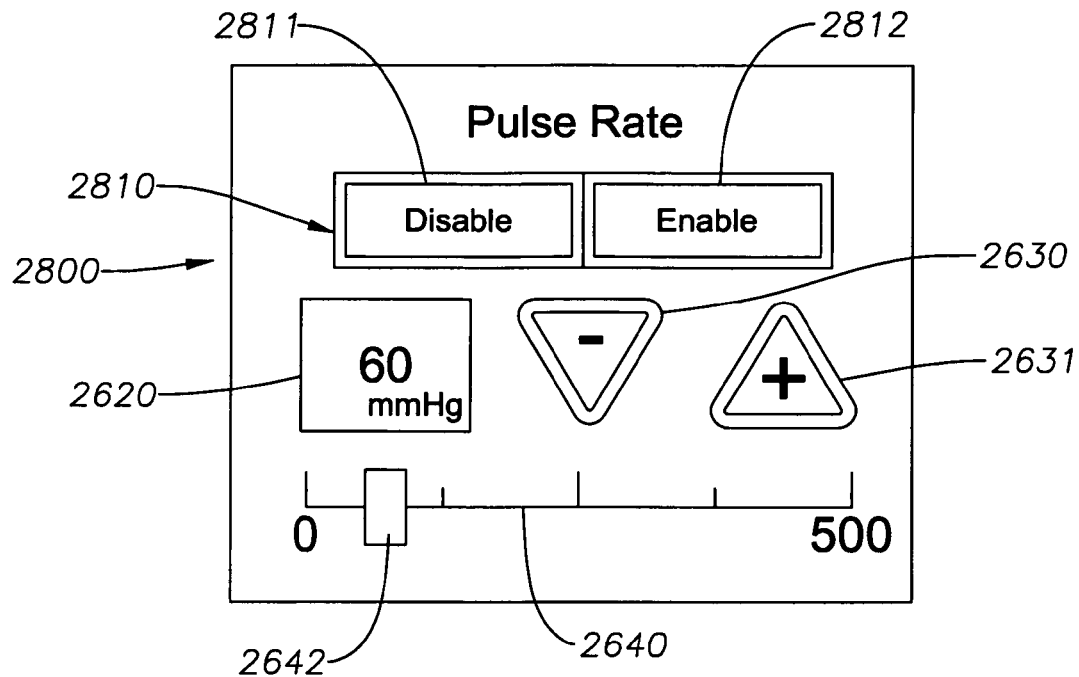
FIG. 28 illustrates a further window embodiment that includes a slide bar and enable buttons.

Referring to FIG. 28, a window 2800 can also include an enable element 2810 that allows a user to enable or disable a feature of the surgical system. In the illustrated embodiment, the enable element includes a Disable button 2811 and an Enable button 2812. Further, FIG. 28 illustrates an alternative arrangement of the display element 2620, arrows 2630 and 2631 and slide bar 2640. The window shown in FIG. 28, similar to the window shown in FIG. 26, can fade away or disappear after a pre-determined amount of time of inactivity.

Figure 29:
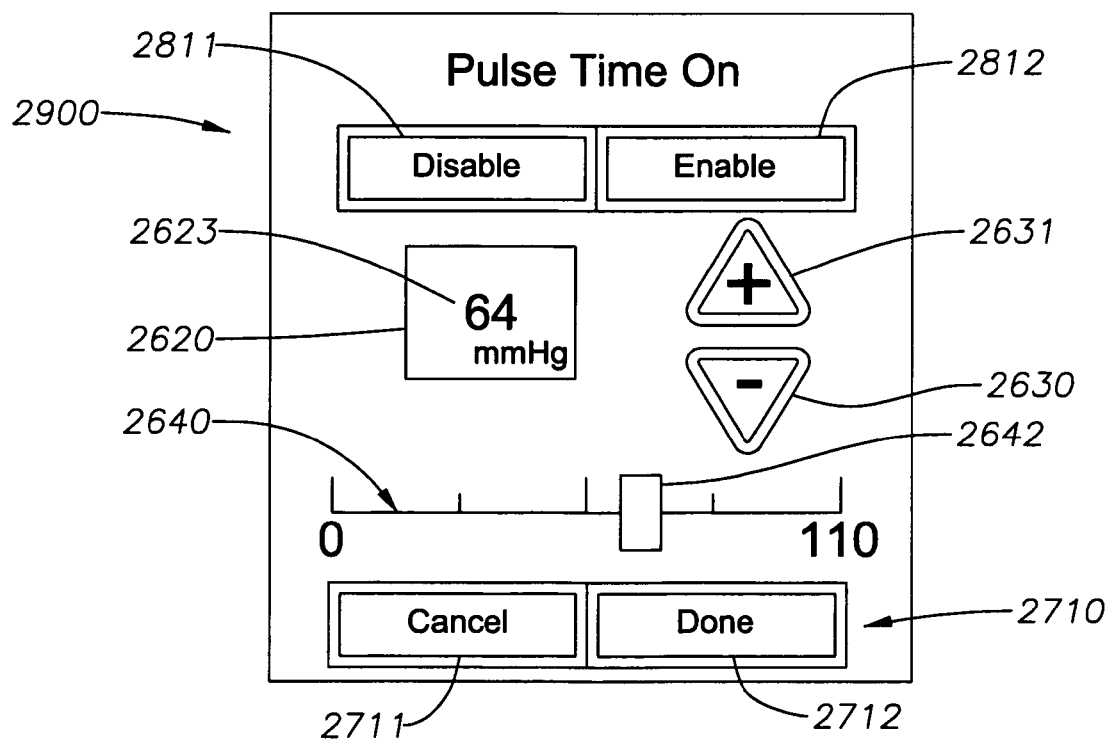
FIG. 29 illustrates yet a further window embodiment that includes an alternative arrangement of components and a selection element that indicates the adjustment is completed.

FIG. 29 illustrates a further window embodiment having a combination of features described above. In particular, the window 2900 shown in FIG. 29 includes a display element 2620, arrows 2630 and 2631, a slide bar 2640, Disable and Enable buttons 2811 and 2812 and Cancel and Done buttons 2711 and 2712. FIG. 29 illustrates yet a further alternative arrangement of these window elements.

Figure 30:
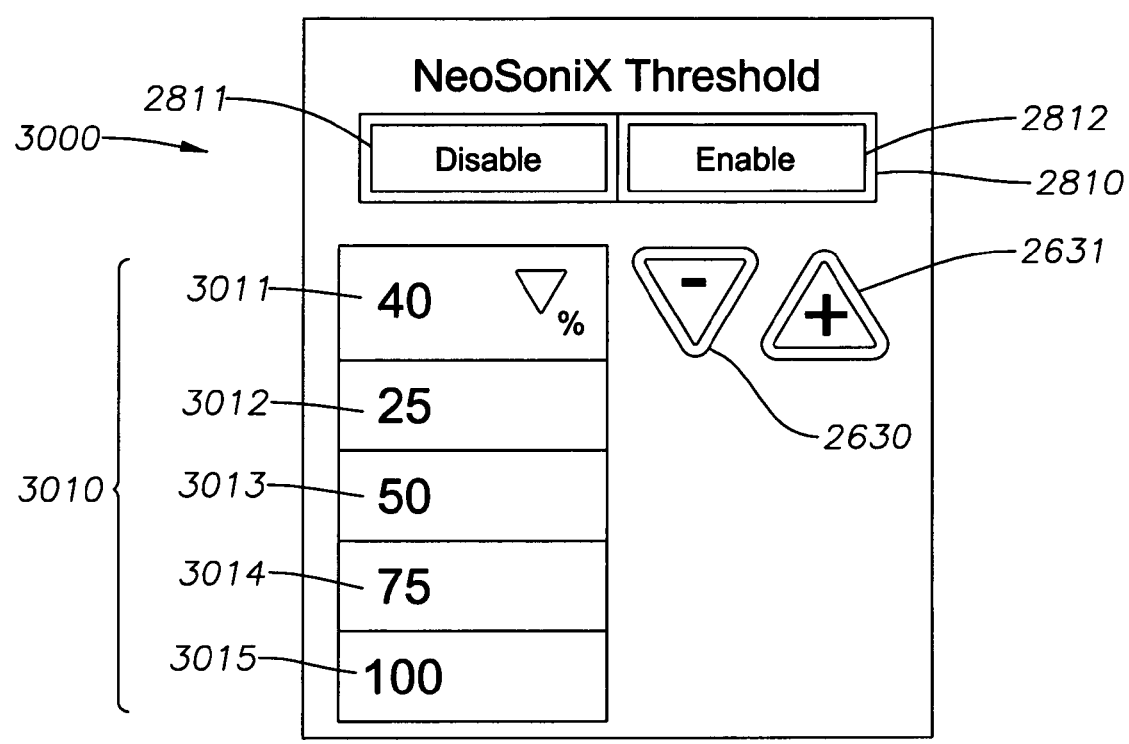
FIG. 30 illustrates another window embodiment that includes a menu of available pulse parameter values.

Referring to FIG. 30, another embodiment of a window 3000 includes a drop down menu or pick list 3010 that includes various values of the parameter that is to be adjusted. As an alternative to the adjustments described above, or as an additional option, a user can select one of the menu options 3011-3015 to select the desired value.

Aspects of a pop-up or dialog windows shown in FIGS. 26-30 can also be applied to pop-up or dialog windows for other surgical procedures, such as phacoemulsification and other procedures. For example, pop-up or dialog windows in a user interface for a phacoemulsification surgical system can fade or disappear after a pre-determined amount of time of inactivity. Alternatively, the user can close a window by pressing a "Done" or other suitable button to indicate that the user has completed the necessary adjustments.

Persons skilled in the art will recognize that the graphical user interface and adjustments to the on-time and the off-time can be modified in various ways. Accordingly, persons skilled in the art will appreciate that embodiments are not limited to the particular exemplary embodiments described, but rather, embodiments can be applied to other surgical equipment and parameters. For example, embodiments can be used with other surgical devices and procedures in addition to phacoemulsification and vitreo-retinal devices, such as coagulation forceps and vitrectomy probes. Although references have been made in the foregoing description to various embodiments, persons skilled in the art will recognize that insubstantial modifications, alterations, and substitutions can be made to the described embodiments without departing from the invention as recited in the accompanying claims.

What is claimed is:

1. A user interface for an ocular surgical system that generates pulses that are adjusted in response to a controller based on settings displayed on a display screen of the ocular surgical system, the user interface comprising:
   a display element that is shown on the display screen and that includes a linear or non-linear representation of a function of a parameter of pulses generated by the ocular surgical system relative to a position of the controller; and
   a window that is displayed on the display screen and generated in response to touching the display screen, the window including a display element having a representation of the function of the parameter of the pulses relative to the position of the controller;
   wherein a current representation of the function of the parameter that is displayed in the window is changeable to a different representation in response to touching the display screen at the window or to touching the display screen at the display element in the window.

2. The user interface of claim 1, wherein the window is generated in response to touching the display screen at the display element.

3. The user interface of claim 1, wherein the window includes at least one adjustment element for changing a value of the parameter.

4. The user interface of claim 3, wherein the adjustment element is an arrow or a slide bar.

5. The user interface of claim 3, wherein the adjustment element includes a pair of arrows and a slide bar.

6. The user interface of claim 1, wherein after the parameter is adjusted, the window is closed by touching the display screen at a pre-defined area of the window.

7. The user interface of claim 1, wherein at least three different representations of the function of the parameter are sequentially displayed in the display element in the window by touching the display screen at the display element to scroll through the at least three different representations.

8. The user interface of claim 1, further comprising a value that includes a value of the parameter, wherein the value is displayed in the display element and in the window.

9. The user interface of claim 1, wherein the non-linear representation is an exponential or a polynomial.

10. The user interface of claim 1, wherein the window occupies a portion of the display screen.

11. The user interface of claim 1, wherein the parameter is an ultrasonic or a non-ultrasonic parameter.

12. The user interface of claim 1, wherein the window fades away or closes after a pre-determined amount of time of inactivity.

13. The user interface of claim 1, wherein the window fades or closes in response to a user.

14. The user interface of claim 1, further comprising a menu or list of values of the parameter, wherein the parameter value is adjusted by selecting a new value the menu or list.

15. The user interface of claim 1 being a user interface for a phacoemulsification surgical system.

16. The user interface of claim 1 being a user interface for a vitreo-retinal surgical system.

17. A user interface for an ocular surgical system that generates pulses that are adjusted in response to a controller based on settings displayed on a display screen of the ocular surgical system, the user interface comprising:
  a display element that is displayed on the display screen and includes a linear or non-linear representation of a function of a parameter of pulses generated by the ocular system relative to a position of the controller;
  a window that is displayed on the display screen and generated in response to touching the display screen, the window including:
    a display element that includes a representation of the function of the parameter of the pulses relative to the position of the controller, and
    an adjustment element for changing a value of the parameter represented in the display element, wherein
  a current representation of the function of the parameter is changed to a different representation in response to touching the display screen at the window, a value of the parameter is changed by touching the display screen at the adjustment element, and after the parameter is adjusted, the window is configured to be closed at least by touching the display screen.

18. The user interface of claim 17, wherein a current representation of the function of the parameter that is displayed in the window is changed to a different representation in response to touching the display screen at the window.

19. The user interface of claim 18, wherein a current representation of the function of the parameter displayed in the window is changed to a different representation in response to touching the display screen at the display element in the window.

20. The user interface of claim 17, wherein the adjustment element is an arrow or a slide bar.

21. The user interface of claim 17, wherein the adjustment element includes a pair of arrows and a slide bar.

22. The user interface of claim 17, wherein at least three different representations of the function of the parameter are sequentially displayed in the display element in the window by touching the display screen at the display element to scroll through the at least three different representations.

23. The user interface of claim 17, further comprising a value that includes a value of the parameter, wherein the value is displayed in the display element and in the window.

24. The user interface of claim 17, wherein the non-linear representation is an exponential or a polynomial.

25. The user interface of claim 17, wherein the parameter is an ultrasonic or a non-ultrasonic parameter.

26. The user interface of claim 17, wherein the window fades away or closes after a pre-determined amount of time of inactivity.

27. The user interface of claim 17, further comprising a menu or list of values of the parameter, wherein the parameter value is adjusted by selecting a new value in the menu or list.

28. The user interface of claim 17 being a user interface for a phacoemulsification surgical system.

29. The user interface of claim 17 being a user interface for a vitreo-retinal surgical system.

30. A user interface for an ocular surgical system that generates pulses that are adjusted in response to a controller based on settings displayed on a display screen, the user interface comprising:
  a display element that is displayed on the display screen and includes a linear or non-linear representation of a function of a parameter of the pulses relative to a position of a foot pedal,
  a window that is displayed on the display screen and generated in response to touching the display screen, the window including:
    a display element having a representation of the function of the parameter of the pulses relative to the position of the controller, and
    an adjustment element for changing a value of the parameter,
  wherein at least three representations of the function of the parameter are sequentially displayed in the display element in the window by touching the display screen at the display element in the window to scroll through the at least three representations, the representation that is displayed in the display element in the window being a selected representation of the parameter, and wherein a value of the parameter is changed by touching the display screen at the adjustment element, and after the parameter is adjusted, the window is configured to be closed at least by touching the display screen.

31. The user interface of claim 30, wherein the adjustment element is an arrow or a slide bar.

32. The user interface of claim 30, wherein the parameter is a power, an on-time or an off-time of pulses generated by the ocular surgical system.

33. The user interface of claim 30, wherein the non-linear representation is an exponential or a polynomial.

34. The user interface of claim 30, wherein the window fades away or closes after a pre-determined amount of time of inactivity.

35. The user interface of claim 30, further comprising a menu or list of values of the parameter, wherein the parameter value is adjusted by selecting a new value from the menu or list.

36. The user interface of claim 30 being a user interface for a phacoemulsification surgical system.

37. The user interface of claim 30 being a user interface for a vitreo-retinal surgical system.

* * * * *